(12) United States Patent
Bhuiyan et al.

(10) Patent No.: US 12,115,180 B2
(45) Date of Patent: Oct. 15, 2024

(54) PH RESPONSIVE DRUG CONJUGATED NANOCARRIERS

(71) Applicants: Board of Supervisors of Louisiana State University and Agricultural and Mechanical College, Baton Rouge, LA (US); NDSU Research Foundation, Fargo, ND (US)

(72) Inventors: Md. Shenuarin Bhuiyan, Shreveport, LA (US); Mohiuddin Quadir, Fargo, ND (US)

(73) Assignees: Board of Supervisors of Louisiana State University and Agricultural and Mehcanical College, Baton Rouge, LA (US); NDSU Research Foundation, Fargo, ND (US)

( * ) Notice: Subject to any disclaimer, the term of this patent is extended or adjusted under 35 U.S.C. 154(b) by 0 days.

(21) Appl. No.: 17/188,891

(22) Filed: Mar. 1, 2021

(65) Prior Publication Data
US 2022/0193105 A1    Jun. 23, 2022

Related U.S. Application Data

(60) Provisional application No. 62/983,687, filed on Mar. 1, 2020.

(51) Int. Cl.
| | | |
|---|---|---|
| *A61K 31/7068* | (2006.01) | |
| *A61K 31/282* | (2006.01) | |
| *A61K 31/519* | (2006.01) | |
| *A61K 31/704* | (2006.01) | |
| *A61K 33/243* | (2019.01) | |
| *A61K 47/54* | (2017.01) | |
| *A61K 47/59* | (2017.01) | |
| *A61K 47/60* | (2017.01) | |

(52) U.S. Cl.
CPC ........ *A61K 31/7068* (2013.01); *A61K 31/282* (2013.01); *A61K 31/519* (2013.01); *A61K 31/704* (2013.01); *A61K 33/243* (2019.01); *A61K 47/545* (2017.08); *A61K 47/593* (2017.08); *A61K 47/60* (2017.08)

(58) Field of Classification Search
CPC .............. A61K 31/7068; A61K 47/593; A61K 47/545; A61K 47/60; A61K 33/243; A61K 31/282; A61K 31/519; A61K 31/704

See application file for complete search history.

(56) References Cited

FOREIGN PATENT DOCUMENTS

CN    107596380 B  *  9/2020

OTHER PUBLICATIONS

P. Ray, et al. "PEG-b-poly (carbonate)-derived nanocarrier platform with pH-responsive properties for pancreatic cancer combination therapy," Colloids and Surfaces B: Biointerfaces 174 (2019) 126-135. Available online Oct. 28, 2018. (Year: 2018).*
English translation of CN107596380B. (Year: 2023).*

* cited by examiner

*Primary Examiner* — Michael P Cohen
(74) *Attorney, Agent, or Firm* — Jones Walker LLP

(57) ABSTRACT

The presently disclosed invention relates to products and methods of treating cancer in a patient comprising administering to the patient a pharmaceutically therapeutic dose of a chemotherapeutic, or any pharmaceutically acceptable salt, solvate, or prodrug thereof, conjugated to a nanocarrier. According to a further embodiment, the chemotherapeutic has a primary (1°) amine (—$NH_2$) group in within a pharmaceutical structure of the chemotherapeutic structure. According to a further embodiment, the chemotherapeutic is one of a platinum-based pharmaceutical and an Anthracycline family pharmaceutical. According to a further embodiment, the chemotherapeutic is one of gemcitabine, methotrexate, cisplatin, oxaliplatin, doxorubicin, daunorubicine, idarubicine, and epirubicine. According to a further embodiment, the chemotherapeutic is either attached to the nanocarrier by means that includes covalent bonds or is attached by means that does not included covalent bonds. According to a further embodiment, the nanocarrier is a pH-sensitive nanocarrier.

12 Claims, 28 Drawing Sheets

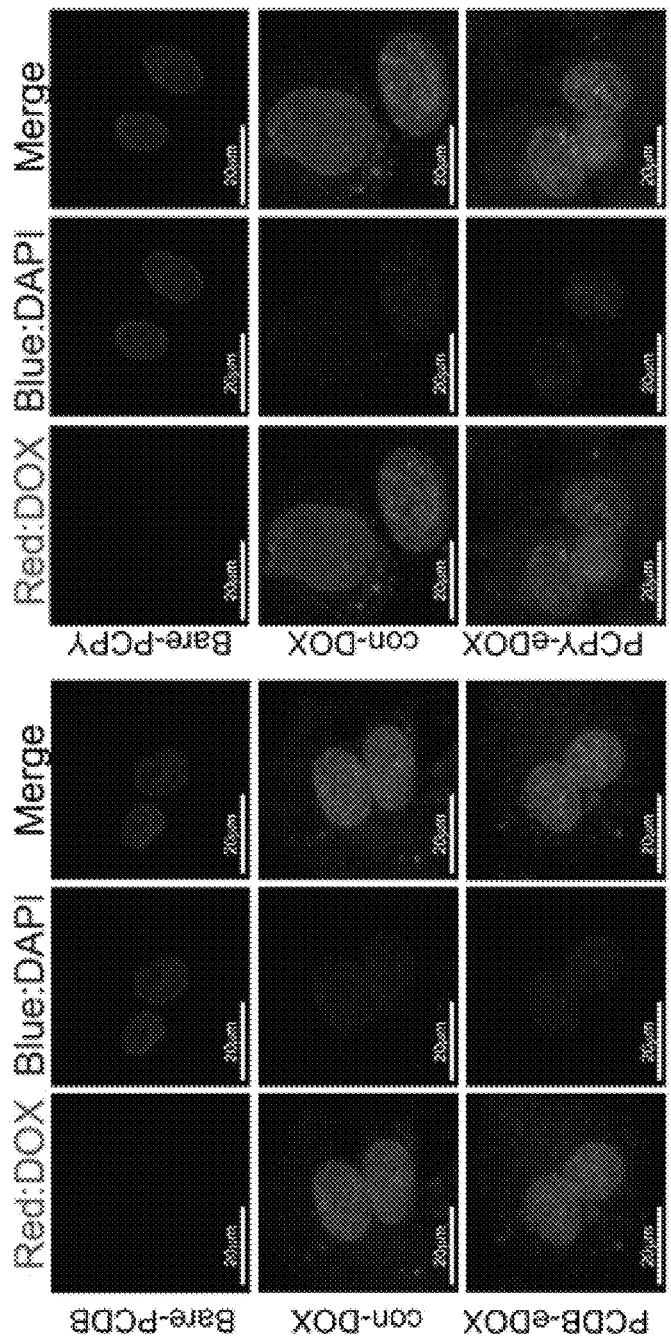
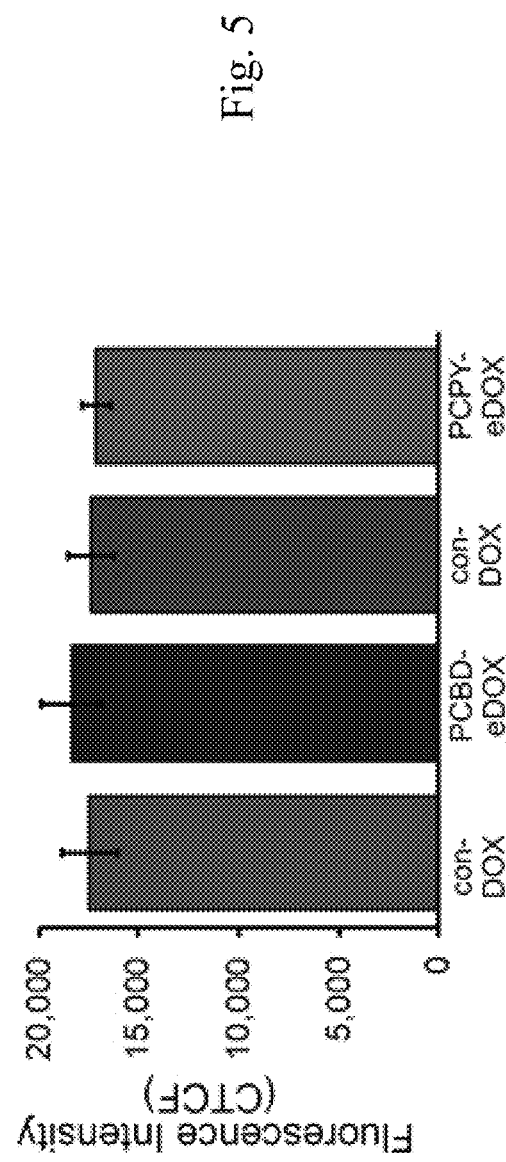
Fig. 5

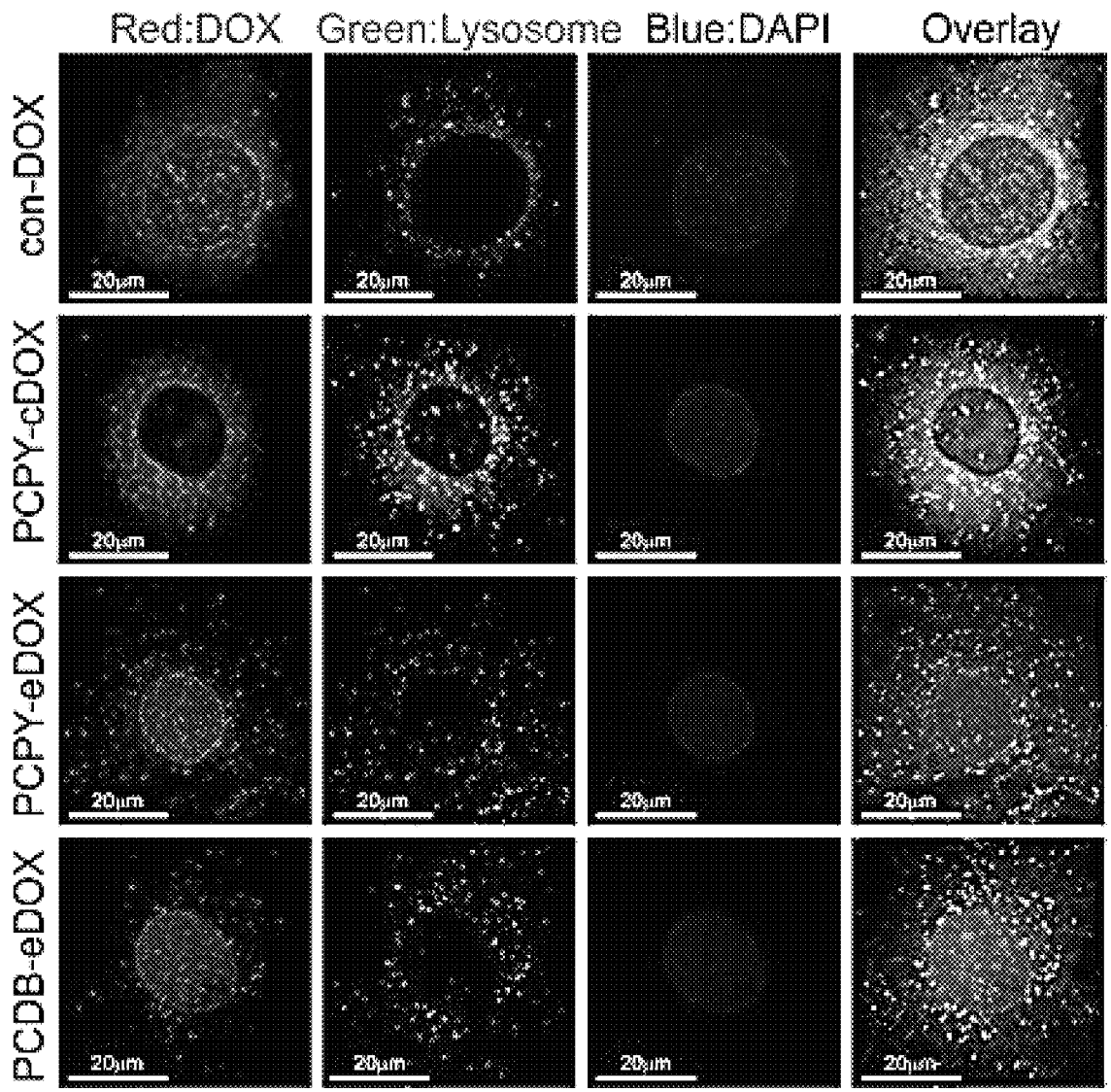
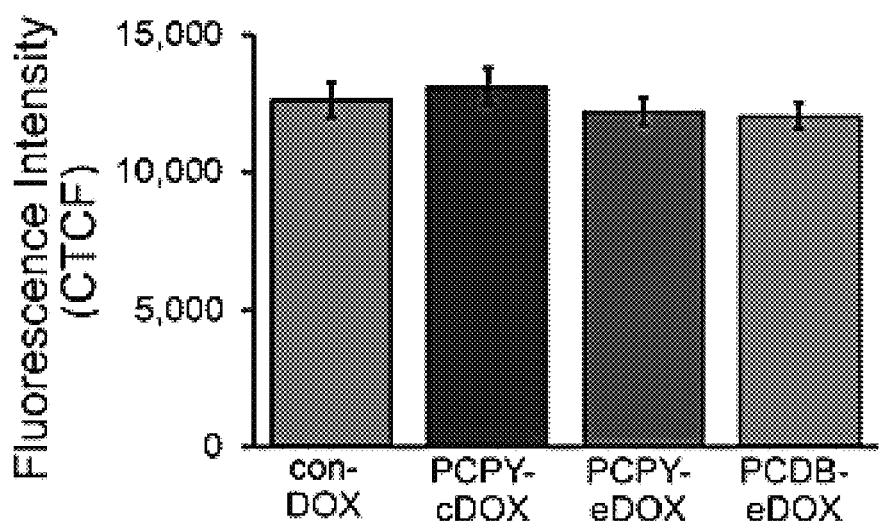
Fig. 9

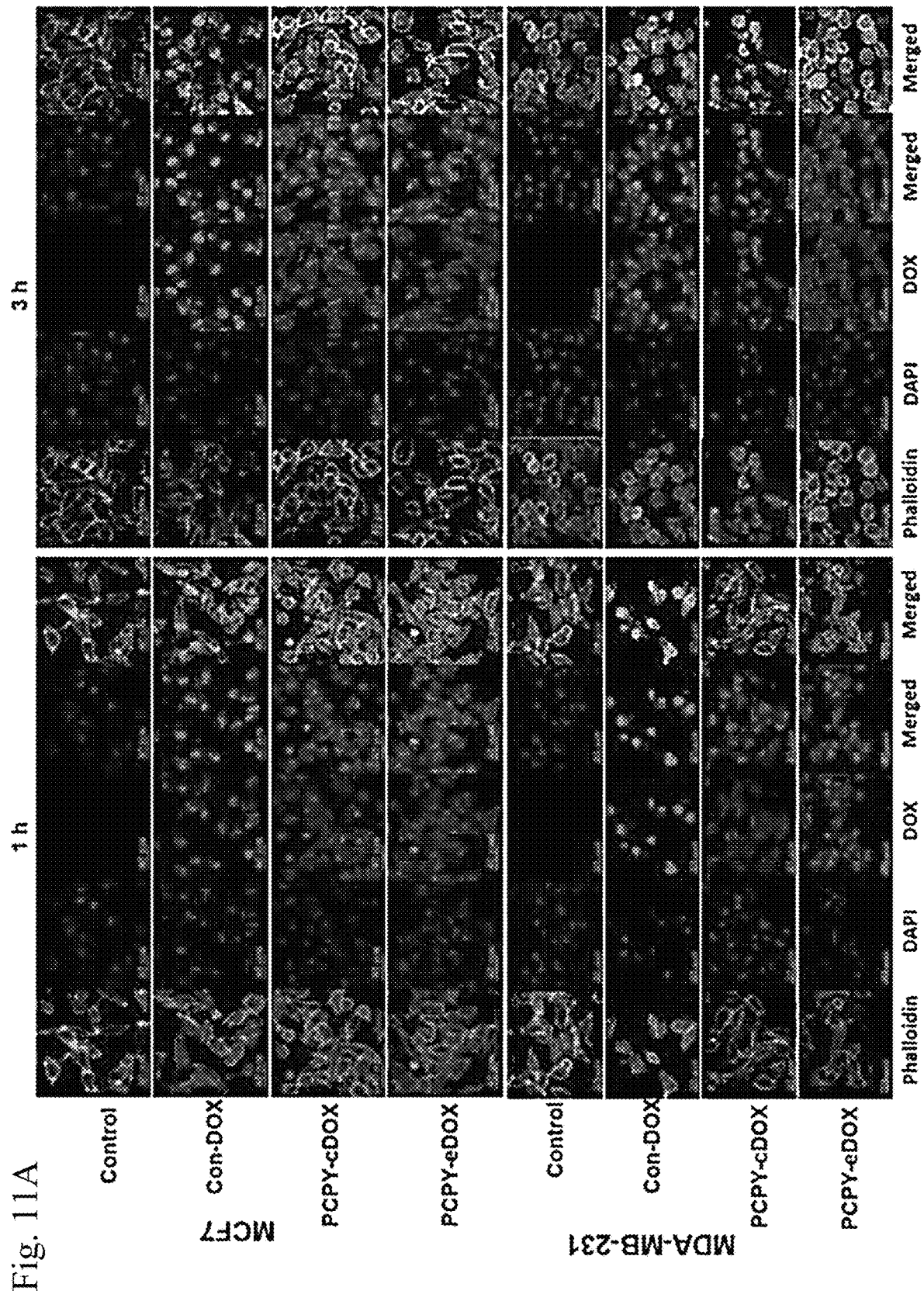

Fig. 16

| PEG-initiated block copolymers | side chains | mode of DOX immobilization | degree of polymerization (DP$_n$) (PC block) | [DOX]$_{mol}$/[polymer]$_{mol}$ |
|---|---|---|---|---|
| PC (3) | N/A | N/A | 18$^a$ | N/A |
| PCPY (4) | 2-pyrrolidine-1-yl-ethyl-amine | N/A | 18$^a$ | N/A |
| PCDB (5) | N,N'-dibutylethylenediamine | N/A | 18$^a$ | N/A |
| PCPY-cDOX (6) | 2-pyrrolidine-1-yl-ethyl-amine + DOX | covalent | 14$^b$ | 5$^c$ |
| PC-cDOX (7) | DOX | covalent | 17$^c$ | 17$^c$ |
| PCHX-cDOX (8) | hexylamine + DOX | covalent | 15$^c$ | 3$^c$ |
| PCPY-eDOX | Encapsulation | encapsulation | N/A | 5$^d$ |
| PCDB-eDOX | Encapsulation | encapsulation | N/A | 4$^d$ |

$^a$Determined by gel permeation chromatography using THF as an eluent. $^b$Determined by gel permeation chromatography using water as an eluent. $^c$Determined by $^1$H NMR spectroscopy. $^d$Determined by UV–vis spectroscopy.

PH RESPONSIVE DRUG CONJUGATED NANOCARRIERS

CROSS REFERENCE TO RELATED APPLICATIONS/PRIORITY

The present invention claims priority to U.S. Provisional Patent Application No. 62/983,687 filed Mar. 1, 2020, which is incorporated by reference into the present disclosure as if fully restated herein. The journal article "Chemical Architecture of Block Copolymers Differentially Abrogate Cardiotoxicity and Maintain the Anticancer Efficacy of Doxorubicin," Chowdhury S. Abdullah, Priyanka Ray, Shafiul Alam, Narendra Kale, Richa Aishwarya, Mahboob Morshed, Debasmita Dutta, Cathleen Hudziak, Sushanta K. Banerjee, Sanku Mallik, Snigdha Banerjee, Md. Shenuarin Bhuiyan, and Mohiuddin Quadir, *Molecular Pharmaceutics* 2020 17 (12), 4676-4690, DOI: 10.1021/acs.molpharmaceut.0c00963 and all references cited in the article, are also incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

STATEMENT REGARDING FEDERALLY SPONSORED RESEARCH OR DEVELOPMENT

This invention was made with government support under Grant Nos. R01 HL145753, P20GM121307 and R00 HL122354 awarded by the National Institutes of Health. The government has certain rights in the invention.

BACKGROUND

Many anticancer drugs or chemotherapeutics are effective at killing cancer cells, but carry the burden of substantial toxicity to other non-cancer cells. Anthracyclines [e.g., doxorubicin (DOX)] are highly effective anticancer drugs, widely used for the treatment of many childhood and adult malignancies, including breast, lung, gastric, ovarian, thyroid, and pediatric cancers, multiple myeloma, and sarcoma. DOX administration develops dose-related cardiomyocyte injury, including aberrant arrhythmias, ventricular dysfunction, and heart failure. The side effects were first described in 1971 in 67 patients treated for a variety of tumors. DOX-cardiomyopathy leads to premature termination of treatment in patients, which increases the likelihood of cancer relapse. Dose- and time-dependent DOX-cardiotoxicity can manifest acutely as well as years after discontinuation of treatment, leading to ventricular dysfunction, dilated cardiomyopathy, and heart failure. Studies showed a correlation between DOX-cardiotoxicity and increased cumulative dose, corresponding to a 5% risk with a cumulative dose of 400 $mg/m^2$, 26% risk with 550 $mg/m^2$, and 48% risk with 700 mg/m Clinically, patients with DOX-cardiotoxicity developed a reduced left ventricular end-diastolic pressure and suppressed the left ventricular ejection fraction because of impaired pumping capacity of the heart, resulting in dilated cardiomyopathy and congestive heart failure. For the foregoing reasons, there is a pressing, but seemingly irresolvable need for developing a method to decrease the toxicity of chemotherapeutics to non-cancer cells, while substantially maintaining effectiveness of the chemotherapeutics on the cancer cells.

SUMMARY

Wherefore, it is an object of embodiments of the present invention to overcome the above-mentioned shortcomings and drawbacks associated with the current technology.

The molecular architecture of pH-responsive amphiphilic block copolymers, their self-assembly behavior to form nanoparticles (NPs), and doxorubicin (DOX)-loading technique govern the extent of DOX-induced cardiotoxicity. The inventors observed that the choice of pH-sensitive tertiary amines, surface charge, and DOX-loading techniques within the self-assembled NPs strongly influence the release and stimulation of DOX-induced cardiotoxicity in primary cardiomyocytes. However, covalent conjugation of DOX to a pH-sensitive nanocarrier through a "conditionally unstable amide" linkage (PCPY-cDOX; PC=polycarbonate and PY=2-pyrrolidine-1-yl-ethyl-amine) significantly reduced the cardiotoxicity of DOX in cardiomyocytes as compared to noncovalently encapsulated DOX NPs (PCPY-eDOX). When these formulations were tested for drug release in serum-containing media, the PCPY-cDOX systems showed prolonged control over drug release (for ~72 h) at acidic pH compared to DOX-encapsulated nanocarriers, as expected. The inventors found that DOX-encapsulated nanoformulations triggered cardiotoxicity in primary cardiomyocytes more acutely, while conjugated systems such as PCPY-cDOX prevented cardiotoxicity by disabling the nuclear entry of the drug. Using 2D and 3D (spheroid) cultures of an ER+breast cancer cell line (MCF-7) and a triple-negative breast cancer cell line (MDA-MB-231), the inventors unravel that, similar to encapsulated systems (PCPY-eDOX-type), the PCPY-cDOX system suppresses cellular proliferation in both cell lines and enhances trafficking through 3D spheroids of MDA-MB-231 cells. Hence, being conjugated and not being encapsulated appears to confer an advantage with respect to lack of toxicity to non-cancer cells. Collectively, the inventors' studies indicate that PCPY-cDOX is less cardiotoxic as compared to noncovalently encapsulated variants without compromising the chemotherapeutic properties of the drug. Thus, the inventors' studies suggest that the appropriate selection of the nanocarrier for DOX delivery may prove fruitful in shifting the balance between low cardiotoxicity and triggering the chemotherapeutic potency of DOX.

The presently disclosed invention relates to products and methods of treating cancer in a patient comprising administering to the patient a pharmaceutically therapeutic dose of a chemotherapeutic, or any pharmaceutically acceptable salt, solvate, or prodrug thereof, conjugated to a nanocarrier. According to a further embodiment, the chemotherapeutic has a primary (1°) amine (—$NH_2$) group in within a pharmaceutical structure of the chemotherapeutic structure. According to a further embodiment, the chemotherapeutic is one of a platinum-based pharmaceutical and an Anthracycline family pharmaceutical. According to a further embodiment, the chemotherapeutic is one of gemcitabine, methotrexate, cisplatin, oxaliplatin, doxorubicin, daunorubicine, idarubicine, and epirubicine. According to a further embodiment, the chemotherapeutic is either attached to the nanocarrier by means that includes covalent bonds or is attached by means that does not included covalent bonds. According to a further embodiment, the nanocarrier is a pH-sensitive nanocarrier. According to a further embodiment, the chemotherapeutic is covalently conjugated to the nanocarrier. According to a further embodiment, the chemotherapeutic is covalently conjugated to the nanocarrier by a conditionally unstable amide bond. According to a further embodiment, the nanocarrier contains 2-pyrrolidine-1-yl-ethyl-amine and a polycarbonate. According to a further embodiment, the nanocarrier releases the chemotherapeutic substantially only in an acidic environment. According to a further embodiment, the cancer has an acidic microenvironment. According to a further embodiment, the cancer is a one of breast, lung, gastric, ovarian, thyroid, multiple myeloma, sarcoma, and pediatric cancers, and the patient is a human.

The presently disclosed invention further relates to methods and pharmaceutical compositions comprising a chemotherapeutic, or any pharmaceutically acceptable salt, solvate, or prodrug thereof, conjugated to a PEG-PC block copolymer nanocarrier. According to a further embodiment, the chemotherapeutic has a primary (1°) amine (—NH$_2$) group in within a pharmaceutical structure of the chemotherapeutic structure. According to a further embodiment, the chemotherapeutic is one of gemcitabine, methotrexate, cisplatin, oxaliplatin, doxorubicin, daunorubicine, idarubicine, and epirubicine. According to a further embodiment, the chemotherapeutic is covalently conjugated to the nanocarrier by a conditionally unstable amide bond. According to a further embodiment, the nanocarrier contains 2-pyrrolidine-1-yl-ethyl-amine and a polycarbonate. According to a further embodiment, the chemotherapeutic is doxorubicin.

According to a further embodiment, the chemotherapeutic nanocarrier conjugate has a formula of:

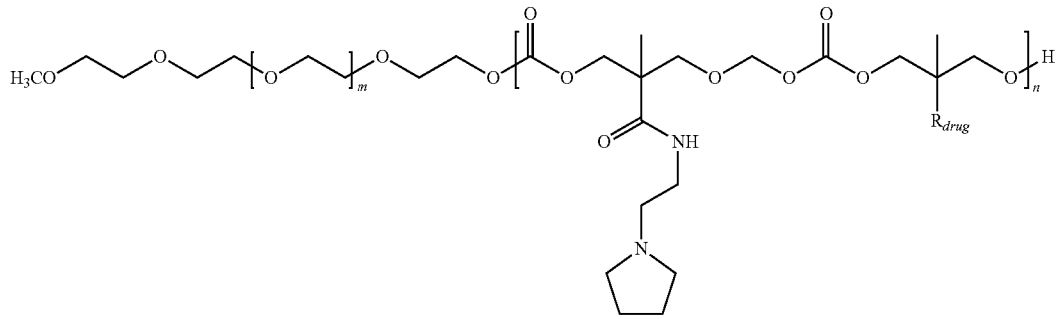

where m is a positive integer between 86 and 142, n is a positive integer between 10 and 40, and $R_{Drug}$ is the chemotherapeutic, or any pharmaceutically acceptable salt, solvate, or prodrug thereof.

The presently disclosed invention further relates to methods and pharmaceutical compositions comprising a chemotherapeutic covalently conjugated to a pH-sensitive nanocarrier conditionally unstable amide bond, wherein the chemotherapeutic is one of gemcitabine, methotrexate, cisplatin, oxaliplatin, doxorubicin, daunorubicine, idarubicine, and epirubicine, or any pharmaceutically acceptable salt, solvate, or prodrug thereof, and the nanocarrier contains 2-pyrrolidine-1-yl-ethyl-amine and a polycarbonate.

The presently disclosed invention further relates to methods of carrying compounds and a nanocarrier comprising a compound having a chemical structure of:

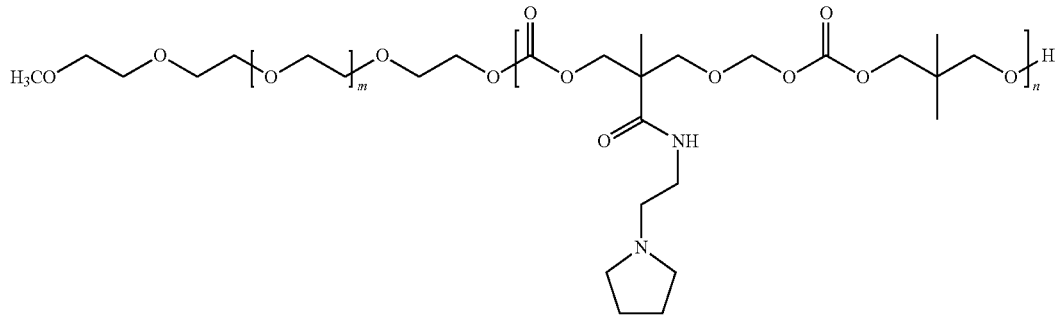

where m is a positive integer between 86 and 142, n is a positive integer between 10 and 40.

The present invention relates to pharmaceutical compositions of a therapeutic (e.g., a chemotherapeutic having a primary (1°) amine (—NH$_2$) group in within the chemotherapeutic's pharmaceutical structure), or a pharmaceutically acceptable salt, solvate, ester, amide, clathrate, stereoisomer, enantiomer, prodrug or analogs thereof, conjugated to a nanocarrier, and use of these compositions for the treatment of a cancer, including cancers with acidic microenvironments that are known to those in the art, such as breast cancers for example.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 μM-10 μM (e.g., between 0.05 μM-5 μM).

In some embodiments, the peak plasma concentration of the therapeutic is maintained for up to 14 hours. In other embodiments, the peak plasma concentration of the therapeutic is maintained for up to 1 hour.

In some embodiments, the condition is a cancer.

In certain embodiments, the cancer is mild to moderate cancer.

In further embodiments, the cancer is moderate to severe cancer.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more additional therapeutic agents for the treatment or prevention of the cancer.

In some embodiments, the therapeutic, or a pharmaceutically acceptable salt, solvate, or prodrug thereof, is administered as a pharmaceutical composition that further includes a pharmaceutically acceptable excipient in addition to the nanocarrier.

In some embodiments, administration of the pharmaceutical composition to a human results in a peak plasma concentration of the therapeutic between 0.05 μM-10 μM (e.g., between 0.05 μM-5 μM).

In some embodiments, the peak plasma concentration of the therapeutic is maintained for up to 14 hours. In other embodiments, the peak plasma concentration of the therapeutic is maintained for up to 1 hour.

In other embodiments, the therapeutic is administered at a dose that is between 0.05 mg-5 mg/kg weight of the human.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active agent (e.g., a therapeutic as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably include a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 μM, 0.1-10 μM, 0.1-5.0 μM, or 0.1-1 μM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release" includes where the agent (e.g., therapeutic), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing a compound described herein (e.g., a chemotherapeutic having a primary (1°) amine (—NH$_2$) group in within the chemotherapeutic's pharmaceutical structure such as gemcitabine, methotrexate, platinum-based drugs, such as cisplatin or oxaliplatin, Anthracycline family (doxorubicin, daunorubicine, idarubicine, epirubicine), for example, or any pharmaceutically acceptable salt, solvate, or prodrug thereof), conjugated to a nanocarrier, and typically manufactured or sold with the approval of a governmental regulatory agency as part of a therapeutic regimen for the treatment of cancer in a mammal.

Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes the nanocarrier and any ingredient other than the compounds described herein (for example, a vehicle capable of suspending or dissolving the active compound) and having the properties of being nontoxic and non-inflammatory in a patient, so long as the other excipient does not substantially interfere with the therapeutic effectiveness of the chemotherapeutic nanocarrier conjugate. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecyl sulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., a cancer), and can also mean treating a pre-disease condition that is a precursor for the disease. Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of therapeutic. A thorough discussion is provided in T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, each of which is incorporated herein by reference. Preferably, prodrugs of the compounds of the present invention are pharmaceutically acceptable.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also include delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" includes the amount of therapeutic present in the plasma of a treated subject (e.g., as measured in a rabbit using an assay described below or in a human).

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 3A shows DLS of NPs resulting from the self-assembly of drug-encapsulated polymer (4, PCPY-eDOX) and (5, PCDB-eDOX) as well as of the drug-conjugated polymer (6, PCPY-cDox). FIG. 3B shows the corresponding zeta potential values of nanosystems, PCPY-eDOX, PCDB-eDOX, and PCPY-cDOX. FIGS. 3C-3E show TEM images of DOX-loaded NPs obtained from (C) PCPY-eDOX, (D) PCDB-eDOX, and (E) PCPY-cDOX systems.

FIG. 5 is confocal fluorescence microscopic images showing DOX distribution in cardiomyocytes in vitro (10 µM, 24 h). Confocal microscopy images show that both the PCDB-eDOX and PCPY-eDOX release DOX ultimately causing nuclear localization like that of con-DOX. The vehicle, bare-PCDB, and bare-PCPY show no effect. The bottom panel shows the corresponding CTCF analysis for the images.

FIG. 6A shows representative Western blot and densitometric quantitation showing increased p53 expression in NRCs. FIG. 6B shows DOX-induced LDH release in NRCs. FIG. 6C shows representative Western blot and densitometric quantitation showing increased LC3II expression in NRCs. Bars represent mean±SEM; n=3 experiments.

FIG. 8A shows representative Western blot and densitometric quantitation showing increased p53 expression in NRCs. FIG. 8B shows DOX-induced LDH release in NRCs. FIG. 8C shows representative Western blot and densitometric quantitation showing increased LC3II expression in NRCs. Bars represent mean±SEM; n=3 experiments.

FIG. 9 is Confocal fluorescence microscopic images showing lysosomal uptake of DOX in cardiomyocytes in vitro (10 µM, 2 h). Confocal images showing the con-DOX, PCDB-eDOX, PCPY-eDOX, and PCPY-cDOX uptake and localization in lysosomes on cardiomyocytes. The bottom panel shows the corresponding CTCF analysis for the images.

FIG. 11A is confocal fluorescence microscopic images of monolayer culture of (top panel) MCF7 cells and (lower panel) MDA-MB-231 cells showing cellular uptake of different samples at 1 and 3 h.

FIG. 16 is a table of composition of DOX-conjugated polymers.

DETAILED DESCRIPTION

Figure 1:
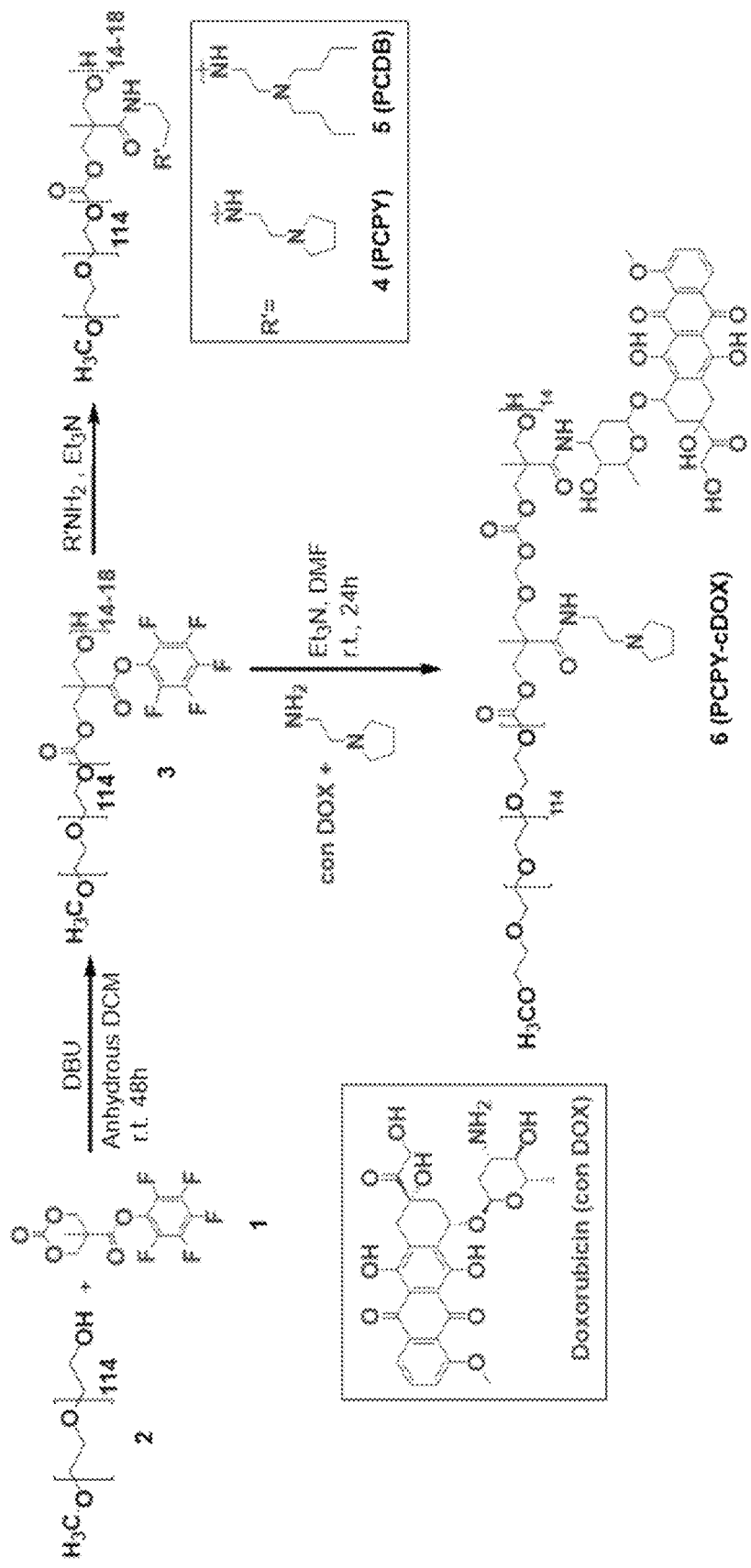
FIG. 1 is a schematic of a synthetic route toward various block copolymers for preparing DOX-NCs, with compounds 1-6 identified therein. All compound number references in the disclosure are to the compounds as depicted in FIG. 1, except where noted differently.
Figure 2:
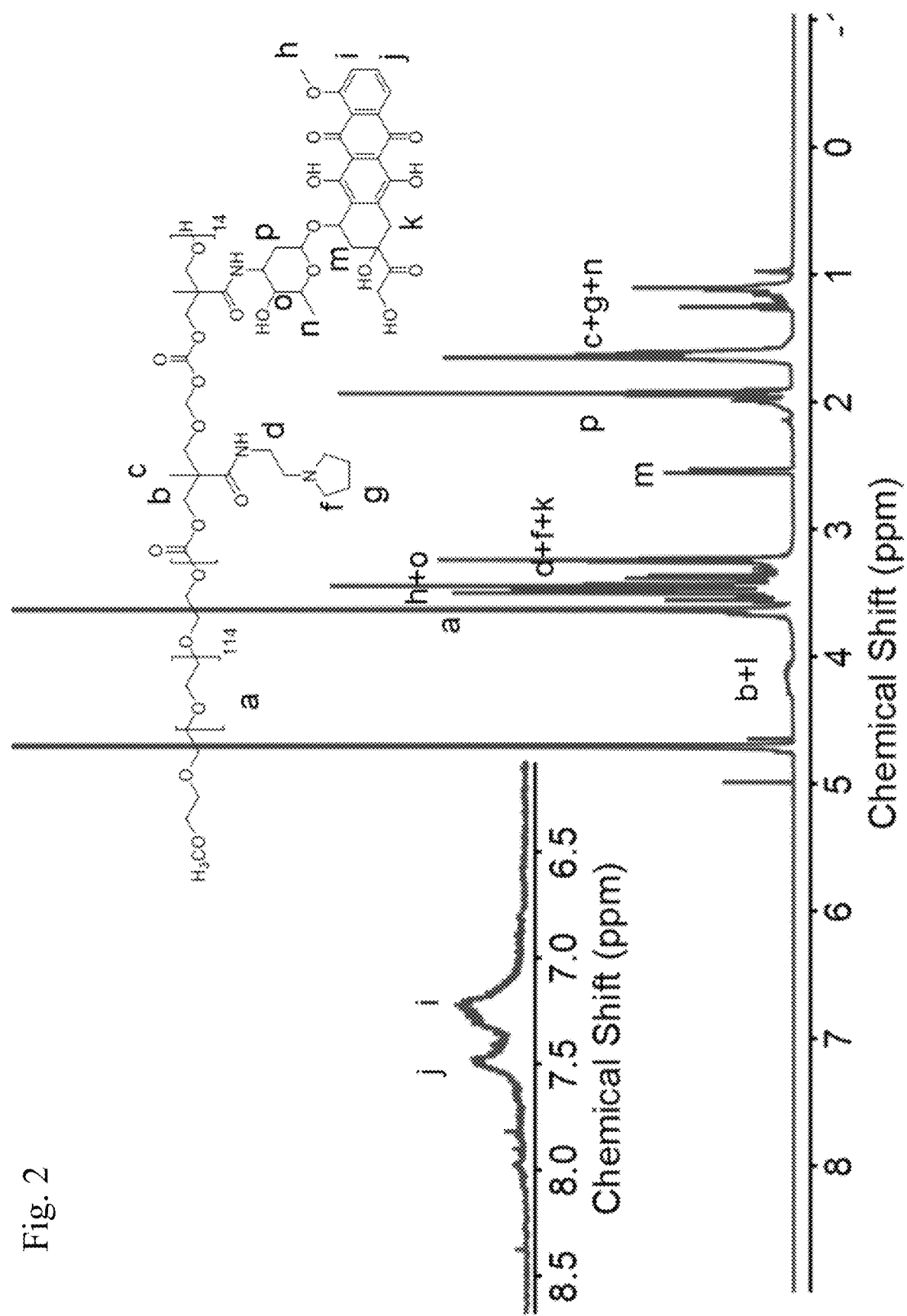
FIG. 2 is a 1H NMR spectrum of PCPY-cDOX in D20 showing the characteristic peaks of DOX.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-27, a brief description concerning the various components of the present invention will now be briefly discussed.

To bypass the toxic effects of DOX, liposome-assisted formulations, such as Doxil (or Myocet) or PEGylated liposomes of DOX have been developed and extensively studied. These formulations are now commercially available and used for treating metastatic breast cancer as the primary therapy. Fundamentally, liposomal systems significantly reduced off-target accumulation of DOX in the heart and suppressed DOX-induced untoward cardiac activity to a significant extent. Numerous polymer-encapsulated or polymer-conjugated systems have also been formulated, which were found to prolong the plasma half-life and show higher efficacy of DOX in clinical and preclinical settings. Despite extensive studies during the past half-century, the molecular signaling pathways that underlie in the cardiotoxic effects of DOX remain obscure and those of polymer-assisted formulations remain under investigated. The pathogenesis of DOX-associated cardiomyopathy is a multifocal disease process whose pathological sequelae involve mitochondrial dysfunction, increased reactive oxygen species production, defects in iron handling, and contractile failure. Recently, the inventors reported that both acute and chronic DOX-cardiomyopathy result from autophagosome accumulation, altered expression of mitochondrial dynamics, oxidative phosphorylation regulatory proteins, and mitochondrial respiratory dysfunction. Similar challenges in the understanding of cardiotoxic effects of DOX also persist when the drug is delivered via polymeric assemblies, and there is a scarcity of knowledge on how the mode of drug encapsulation inside polymeric nanocarriers (NCs) modulate cardiac toxicity within primary myocytes. Therefore, the primary goal of this study is to design a modular, DOX-loaded, pH-sensitive nanocarrier using amphiphilic block copolymers (FIG. 1) and to use this construct to understand how structural elements of the copolymer control cardiac toxicity. The inventors showed that, while breast cancer cells were efficiently affected by DOX immobilized in pH-responsive polymeric NCs, no drug-associated toxicity was evident only for DOX-conjugated NCs in cardiac myocytes at cytosolic and nuclear levels. The inventors envision that the inventors' results will shed new light on the structure—activity relationship of stimuli-responsive NCs of DOX and how the molecular diversity of carrier systems protects and rescues cardiac cells from DOX-associated toxicity.

EXPERIMENTAL SECTION: Materials. All chemicals were purchased from Sigma-Aldrich, and anhydrous solvents were purchased from VWR, EMD Millipore. DOX hydrochloride was purchased from LC Laboratories. $^1$H and $^{13}$C NMR spectra were recorded using a Bruker 400 MHz spectrometer using TMS as the internal standard. Infrared (IR) spectra were recorded using an ATR diamond tip on a Thermo Scientific Nicolet 8700 FTIR instrument. Dynamic light scattering (DLS) measurements were carried out using a Malvern instrument (Malvern ZS 90). UV-visible and fluorescence spectra were recorded using a Varian UV-vis spectrophotometer and a Fluorolog3 fluorescence spectrophotometer, respectively. Transmission electron microscopy (TEM) studies were carried out using a JEOL JEM2100 LaB6 transmission electron microscope (JEOL USA) with an accelerating voltage of 200 keV. 3D spheroid cultures were grown using the n3D kit purchased from Greiner Bio.

Cell Lines and Maintenance. Primary Neonatal Rat Cardiomyocyte Culture. The inventors isolated neonatal rat cardiomyocytes (NRCs) from the ventricles of 1-2 day old Sprague Dawley rat pups as described previously. Briefly, ventricular tissues excised from rat pups were digested with collagenase at 4° C. overnight with subsequent digestion in trypsin. Next, cells were preplated to remove cardiac fibroblasts, followed by plating of isolated cardiomyocytes at $1.5 \times 10^6$ cells per 10 cm$^2$ plate in αMEM containing 10% fetal bovine serum (FBS) (Gibco) and 1% antibiotic-antimycotic (Gibco) media. After 24 h, NRCs were maintained in Dulbecco's modified Eagle's medium (DMEM) (Gibco) containing 2% FBS and 1% antibiotic-antimycotic and subjected to different treatments, as described previously. All cell culture treatments were repeated in three independent experiments.

Breast Cancer Cell Lines. Two different breast cancer cell lines from ATCC, viz., MCF7 (ER+) and MDA-MB-231 (triple-negative), have been used in this study. The cells were grown in DMEM (HyClone, GE Healthcare Life Sciences), supplemented with 10% FBS (HyClone, GE Healthcare Life Sciences) and 1% penicillin-streptomycin (Gibco)

Figure 17:
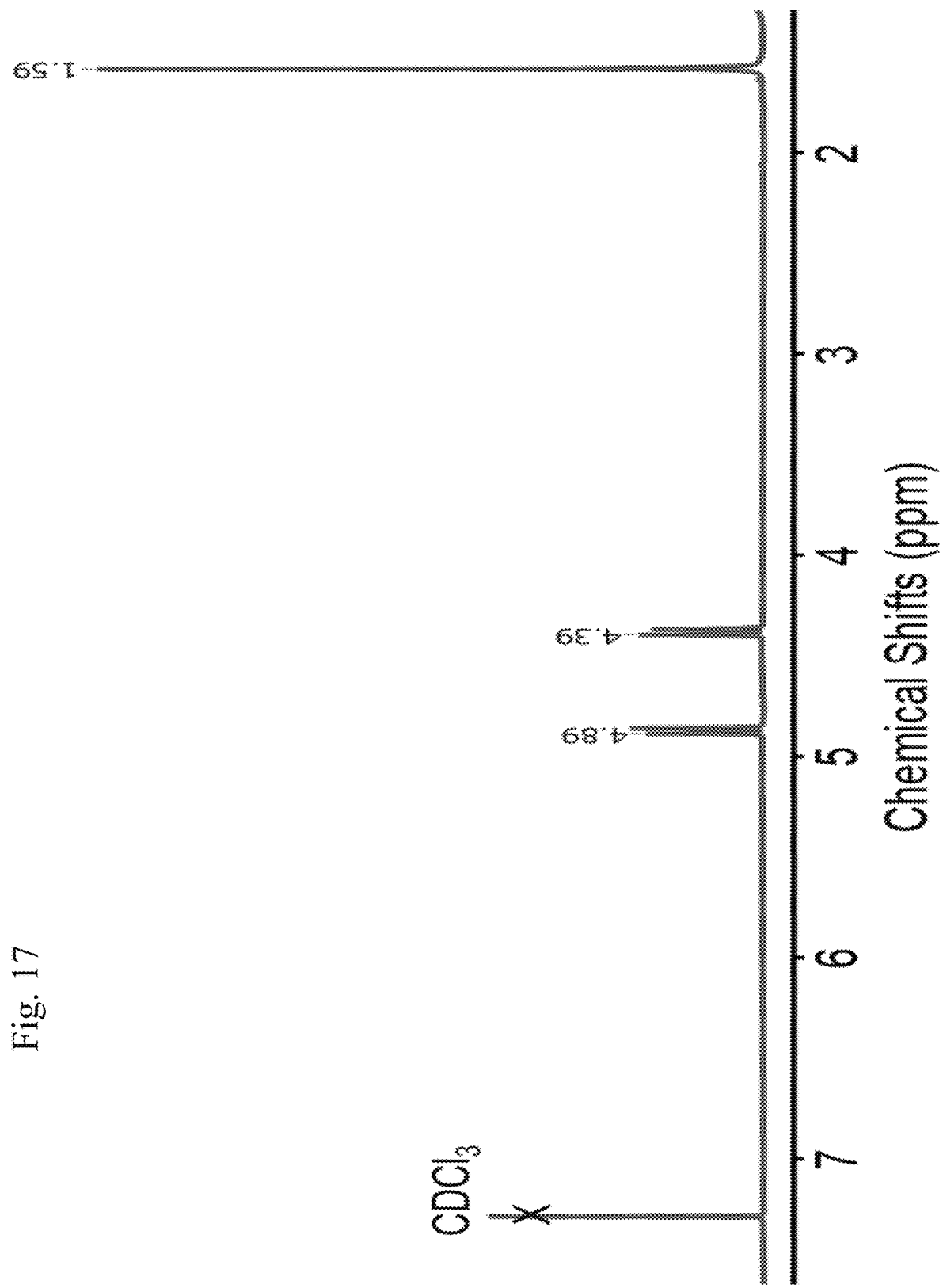
FIG. 17 is a 1H NMR spectrum of the monomer (FIG. 14 compound 1). 1H NMR (400 MHz, CDCl3, TMS): δ(ppm)= 4.88 (d, 2H, CHaHb), 4.39 (d, 2H, CHaHb), 1.59 (s, 3H, CCH3).

Synthesis of PEG-b-poly(carbonate). PEG-b-poly-(carbonates) (PEG-b-PC) was synthesized using poly(ethylene glycol) (PEG, $M_n$=5000 g/mol) as the initiator via ring-opening polymerization of a monomer, viz., a pentafluorophenyl-protected bis(methoxy propionic acid) derivative. The synthesis of the monomer was performed as follows (FIG. 13): 21.7 g (55 mmol) of bis-(pentafluorophenyl) carbonate, 3 g (22 mmol) of 2,2-bis(hydroxymethyl)propionic acid (bis-MPA), and 0.7 g (4.6 mmol) of CsF were dissolved in 70 mL of anhydrous tetrahydrofuran (THF), and the reaction mixture was stirred at room temperature for 20 h. The solvent was removed in vacuo, and the residue was redissolved in dichloromethane (DCM), following which a white precipitate was filtered off. The filtrate was extracted with sodium bicarbonate and water and was dried over MgSO$_4$. The solvent was evaporated under vacuum. The product was recrystallized from a 1:1 (v/v) mixture of ethyl acetate/hexane to give the pentafluorophenyl ester as white crystals, which were filtered and dried in a desiccator and analyzed by $^1$H NMR (FIG. 17). PEG-b-PC block copolymers were synthesized following a procedure described earlier (FIG. 1). Briefly, 30 mg (0.006 mmol) of mPEG-OH (2) and 100 mg (0.3 mmol) of monomer (1) were dissolved in 3 mL anhydrous DCM under nitrogen, and then 1,8-Diazabicyclo[5.4.0]undec-7-ene (10.19 mg, 0.06 mmol) was added to the solution to facilitate polymerization. After stirring for 48 h at room temperature, the reaction was quenched by precipitating into diethyl ether and centrifuging at 7000 rpm (~5040 g) for 30 min. The supernatant was decanted, an equal volume of diethyl ether was added, and the solution was recentrifuged for another 30 min at the same speed to yield the polycarbonate block (3). The synthesized intermediate block copolymer, polycarbonate (PC, compound 3), was aminated with 2-pyrrolidine-1-yl-ethyl-amine (PY) to generate PCPY (compound 4) and N,N'-dibutylethylenediamine (DB) to generate PCDB (compound 5) in DMF at room temperature for 24 h. These compounds have been characterized and purified according to previously published reports.

Synthesis of Drug-Conjugated Polymers. Copolymer 4 (PCPY) was selected for drug conjugation because of its p$K_a$, which is more conducive to protonation at the endosomal pH. To synthesize the drug-polymer conjugate, the inventors covalently attached primary amine-containing drug molecules via an amide linkage to the polymer backbone. Briefly, 100 mg (0.0075 mmol) of (3) was dissolved in 5 mL DMF and cooled in an ice bath; to this, 0.5 mL of DMF solution containing 23 mg (0.038 mmol) of DOX hydrochloride, 45 µL (0.34 mmol) of 2-pyrrolidine-1-yl-ethyl-amine, and a catalytic amount of triethylamine were added dropwise with constant stirring. The solution was brought to room temperature and allowed to stir for 24 h, followed by precipitation in a large excess of cold diethyl ether to generate PCPY systems covalently connected with DOX (PCPY-cDOX) (compound 6). The PCPY-cDOX conjugate was characterized by $^1$H NMR spectroscopy (FIG. 2) and aqueous phase gel permeation chromatography (FIG. 18A). To investigate the conjugation mechanism, two control polymers were prepared. In one system, no pH-sensitive tertiary amine was present, and the hydrophobic backbone of the polymer was stoichiometrically connected with DOX (PC-cDOX, compound 7). In the second control system, a pH nonresponsive amine, such as hexylamine (HX), was connected to the hydrophobic backbone of the polymer along with DOX, yielding PCHX-cDOX systems (compound 8). The synthetic protocol and NMR characterization of these control polymers are presented in FIGS. 14 and 18B. The composition of all synthesized polymers is summarized in FIG. 16.

Quantification of DOX Payload in the Polymer-Drug Conjugate. The PCPY-cDOX (6) system was a lyophilic solute. Therefore, to determine the amount of DOX within the conjugate, PCPY-cDOX (5 mg) was dissolved in 2 mL of a buffer of pH 7.4. After sonication for 30 min, the suspension was filtered through a 0.45 μm PES membrane filter. The amount of DOX in the filtrate was quantified by measuring the absorbance at 495 nm using UV-visible spectroscopy. DOX payload in the conjugate was estimated according to the following equation:

$$\text{payload (\%)} (w/w) = \frac{\text{amount of drug loaded}}{\text{total weight of formulation}} \times 100$$

Particle Size and Zeta Potential Analyses of Nanoparticles. The hydrodynamic diameters of the resulting nanoparticles (NPs) prepared from copolymers PCPY (4), PCDB (5), and PCPY-cDOX (6) were determined using DLS measurements at a scattering angle of 90°. For zeta potential measurements, a sample concentration of 10 mg/mL was used, and the zeta potential was determined in terms of electrophoretic mobility by taking an average of five readings. For all these measurements, the sample solution was filtered using a 0.2 μm PES filter.

Size Analysis Using TEM Imaging. A drop of NP sample [obtained from copolymers PCPY (4), PCDB (5), and PCPY-cDOX (6)] was placed on a 300-mesh formvar-carbon-coated copper TEM grid (Electron Microscopy Sciences) for 1 min and wicked off. Phosphotungstic acid 0.1%, with pH adjusted to 7-8, was dropped onto a grid and allowed to stand for 2 min and then wicked off. NPs have been investigated for their microstructure by TEM at 200 keV.

Preparation of Drug-Loaded NPs. For the preparation of noncovalently encapsulated DOX NPs of block copolymers, either PCPY (4) or PCDB (5) block copolymer (10 mg) was dissolved in 250 μL of DMSO in the presence of 5 mg of DOX hydrochloride. The solutions were added dropwise to a stirred solution of 750 μL of PBS buffer (pH 7.4). The solution was stirred overnight, followed by dialysis using a Float-A-Lyzer (MWCO: 3.5-5 kDa) against 800 mL of PBS buffer (pH 7.4) to generate PCPY- or PCDB-encapsulated DOX, that is, PCPY-eDOX and PCDB-eDOX systems, respectively. These NP suspensions were analyzed using UV-vis spectroscopy for quantification of the amount of drug loading within NPs. For drug encapsulated in NPs, the following formula was used to calculate the encapsulation efficiency ("encap eff"):

$$\text{percent } encap \text{ } eff \text{ (\%)} = \frac{\text{amount of drug added} - \text{amount of drug encapsulated}}{\text{amount of drug added}} \times 100$$

Figure 20:
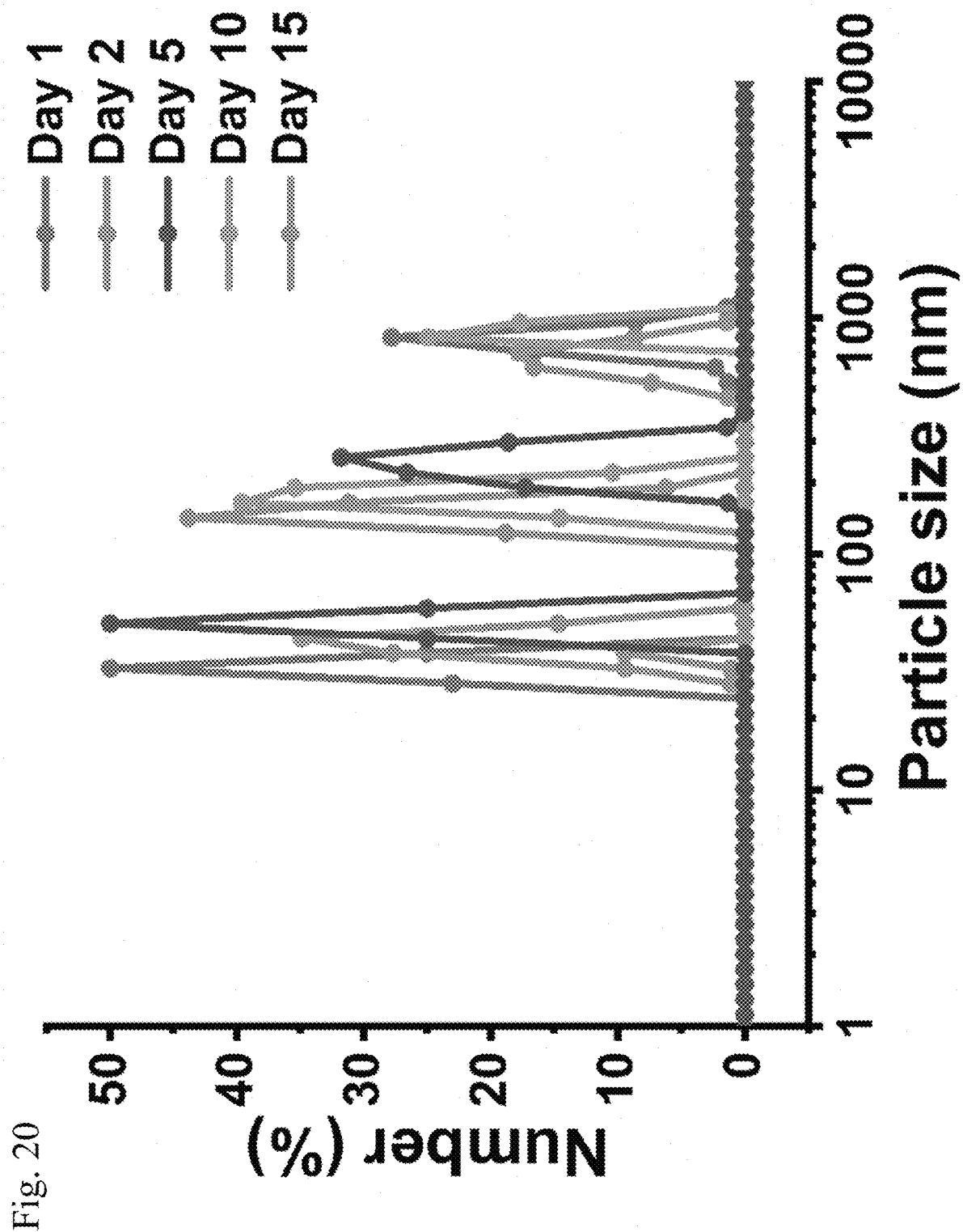
FIG. 20 is chart showing Nanoparticles formed when PCPY-cDOX nanoparticles were directly suspended in PBS of pH 7.4 are not monodispersed. Particle size distribution also increases over time.

For generating NPs from the conjugated system, 10 mg of PCPY-cDOX (6) was dissolved in 250 μL of DMSO, and nanoprecipitated in 750 μL of PBS buffer (pH 7.4). Similar purification processes as described above for noncovalently encapsulated systems were used. It is important to note that PCPY-cDOX (6) is a lyophilic colloid and is soluble in PBS. However, direct dissolution of PCPY-cDOX in water does not yield a uniformly dispersed population of NPs, and the polydispersity of the resulting suspension was found to increase with time (FIG. 20).

In Vitro Drug Release Experiments. Drug release experiments were conducted by taking 1 mL of the drug-loaded NP solution spiked with 10% FBS in a Float-A-Lyzer (MWCO: 3.5-5 kDa). Noncovalently stabilized NP solutions, that is, PCPY-eDOX and PCDB-eDOX systems, as well as polymer-drug conjugated NPs (PCPY-cDOX, 6), were used. The solution was introduced into the inner chamber of the Float-A-Lyzer and the outer chamber was filled with 5 mL of buffer at the desired pH (7.4 and 5.5 for the PCPY and PCPY-cDOX systems and 7.4 and 4.5 for the PCDB system). A specified volume of the bulk solution was withdrawn periodically and replaced by an equal volume of the fresh buffer of similar pH to maintain the sink condition. Of note, pH 4.5 was used to mimic lysosomal pH conditions.

Protein Extraction and Western Blot Analyses. NRCs were washed with PBS and lysed with CelLytic M (Sigma-Aldrich) lysis buffer containing a complete protease inhibitor cocktail (Roche®). Next, the lysed cells were homogenized by sonication and centrifuged at 15,000 g for 10 min at 4° C. to sediment any insoluble material. The protein concentration of the soluble cardiomyocyte lysates was measured using the modified Bradford reagent relative to a BSA standard curve (Bio-Rad®) in a 1 mL cuvette on a DS-11 FX+ spectrophotometer (DeNovix®, Wilmington, DE). Proteins were separated on SDS-PAGE using precast 7.5-15% Criterion Gels (Bio-Rad®) and transferred to PVDF membranes (Bio-Rad®). Membranes were blocked for 1 h in 5% nonfat dried milk and exposed to primary antibodies overnight at 4° C. The following primary antibodies were used for immunoblotting: anti-LC3B (1:1000, 2775, Cell Signaling Technology), anti-p53 (1:1000, sc-1314, Santa Cruz Biotechnology®), and anti-GAPDH (1:1000, MAB374, Sigma-Aldrich®). Membranes were subsequently washed, incubated with alkaline phosphatase-conjugated secondary antibodies (Jackson ImmunoResearch®), developed with ECF reagent (Amersham®), and imaged using ChemiDoc Touch Imaging System (Bio-Rad®). Ponceau S protein staining on the transferred membranes was used to confirm equal loading. Protein band densitometry analyses on scanned membrane images were carried out using NIH ImageJ software (Bethesda, MD).

Biochemical Assays. Lactate Dehydrogenase Release Assay for Cardiac Myocytes. Following treatments, culture media were collected and cleared by centrifugation at 5000 g for 10 min. Lactate dehydrogenase (LDH) release into culture media was measured using a cytotoxicity detection kit (Roche®) as per the manufacturer's instructions. Color development was measured using a microplate absorbance reader at an absorbance of 492 nm (Bio-Rad®).

Cancer Cell Viability Assay. The cytotoxicity of drug-conjugated NPs (PCPY-cDOX, 6) and of the free drug was tested on two different breast cancer cell lines, viz., MCF7 and MDA-MB-231. For this experiment, 5000 cells/well were seeded in 96-well plates and, after 24 h, were treated with different concentrations of drug-conjugated NPs and the equivalent concentration of conventional DOX formulation (free DOX). After incubating the cells for 72 h, cell viability was evaluated by the MTS assay. Cell viability was calculated using the following equation:

$$\text{cell viability}(\%) = \frac{\text{absorbance of test sample}}{\text{absorbance of control}} \times 100$$

Confocal Fluorescence Microscopy. Confocal Microscopy of Cardiac Myocytes. To visualize the subcellular distribution of DOX and the prepared NPs carrying DOX, NRCs were plated on Lab-Tek II chamber slides (Thermo Scientific®, 154461) at a density of $1 \times 10^5$ cells/well. Next, NRCs were treated with DOX (dissolved in DMSO) at 5, 10, and 25 µM for 24 h. NRCs treated with only DMSO served as an experimental control. PCPY-cDOX, PCPY-eDOX and PCDB-eDOX NPs were treated at described concentrations. NPs containing no DOX served as control. After 24 h, NRCs were immediately washed with PBS (pH 7.4) and fixed with 3.7% paraformaldehyde in PBS for 10 min as per manufacturer's instructions (Molecular Probes, Invitrogen®). Nuclei were stained with 2-phenylindole (DAPI) (Invitrogen®). NR s were then mounted with VECTASHIELD® HardSet antifade mounting media for fluorescence (Vector Laboratories®). To assess the intracellular distribution of DOX, cardiomyocytes were subsequently observed on a Nikon® MR high-speed confocal microscope (Nikon Instruments Inc., Melville, NY) using an ×60 oil objective (NA=1.4) and imaged using Nikon® NIS-Elements C software. DOX accumulation was detected using a 561 nm excitation laser coupled to 575-625 nm emission bandwidths on a G sP PMT detector on a Nikon® A1R confocal microscope. In a separate set of experiments, following 2 h of treatment, NRCs were immediately stained with LysoTracker® Deep Red dye (excitation/emission: 647 nm/658 nm), L12492, Molecular Probes, (Invitrogen®) to visualize lysosomes, then fixed, counterstained, and mounted. Lysosomes were then visualized using a far-infrared 640 nm excitation laser with 650-720 nm emission bandwidths on a Nikon® A1R confocal microscope using a ×60 oil objective (NA=1.4). Lysosomes are presented as pseudo-colored green organelles in representative images along with DOX accumulation in red. For all cardiomyocyte treatment groups with DOX and DOX-loaded NPs, DOX distribution in cardiomyocytes was measured (>60-100 cardiomyocytes in each group, with a total of 1270 cardiomyocytes) in the acquired high-magnification red channel microscopy images from three independent experiments through the corrected total cell fluorescence (CTCF) [CTCF=integrated density—(area of selected cardiomyocytes×mean fluorescence of background readings)] assessment using NIH ImageJ (v1.52a) soft-ware. All image observations, acquisitions, and analyses were conducted in an investigator-blinded manner through α-numerical labeling of the slides and images.

Confocal Microscopy of Monolayer and Spheroid Culture of Breast Cancer Cells. MCF7 and MDA-MB-231 cells were seeded onto the ibidi glass-bottom dish (35 mm) at $1 \times 10^5$ cells per well and grown overnight. Cells were then incubated with NPs obtained from PCPY-eDOX and PCPY-cDOX at 37° C. in DMEM high-glucose medium for 1 and 3 h. At the end of this period, cells were washed with PBS, followed by the addition of DAPI and phalloidin, and analyzed using a confocal fluorescence microscope. Spheroid cultures of MCF7 and MDA-MB-231 cells were used to study the penetration and uptake of drug-loaded NPs. To grow these spheroid cultures, cells were grown to 70% confluency and treated with the NanoShuttle® (n3D Biosciences® courtesy Greiner Bio®) solution overnight. Following incubation, the cells were washed, trypsinized, and then seeded in a 96-well plate with a cell-repellent surface (n3D Biosciences® courtesy Greiner Bio®) at a seeding density of $1 \times 10^6$ cells per spheroid. The cells were incubated on the spheroid drive (n3D Biosciences®, Greiner Bio®) at 37° C. overnight in an incubator. After 24 h of incubation, and when the spheroids were visible, they were treated with NPs and incubated for another 24 h. Following this incubation period, the spheroids were washed with PBS (while placed on a holding drive so as not to disrupt the spheroids), stained with DAPI, and analyzed using a confocal fluorescence microscope. The confocal images were obtained using a Zeiss® Axio Observer Z1 microscope equipped with a LSM700 laser scanning module (Zeiss®, Thornwood, NY) at 40× magnification with a 40× at lens.

Statistical Analysis. Data are expressed as mean±SEM. All statistical tests were done with GraphPad Prism (v8.2.1) software (San Diego, CA). Data were analyzed using one-way ANOVA, followed by Tukey's multiple comparisons post hoc test. A P value of less than 0.05 was considered statistically significant.

Figure 18:
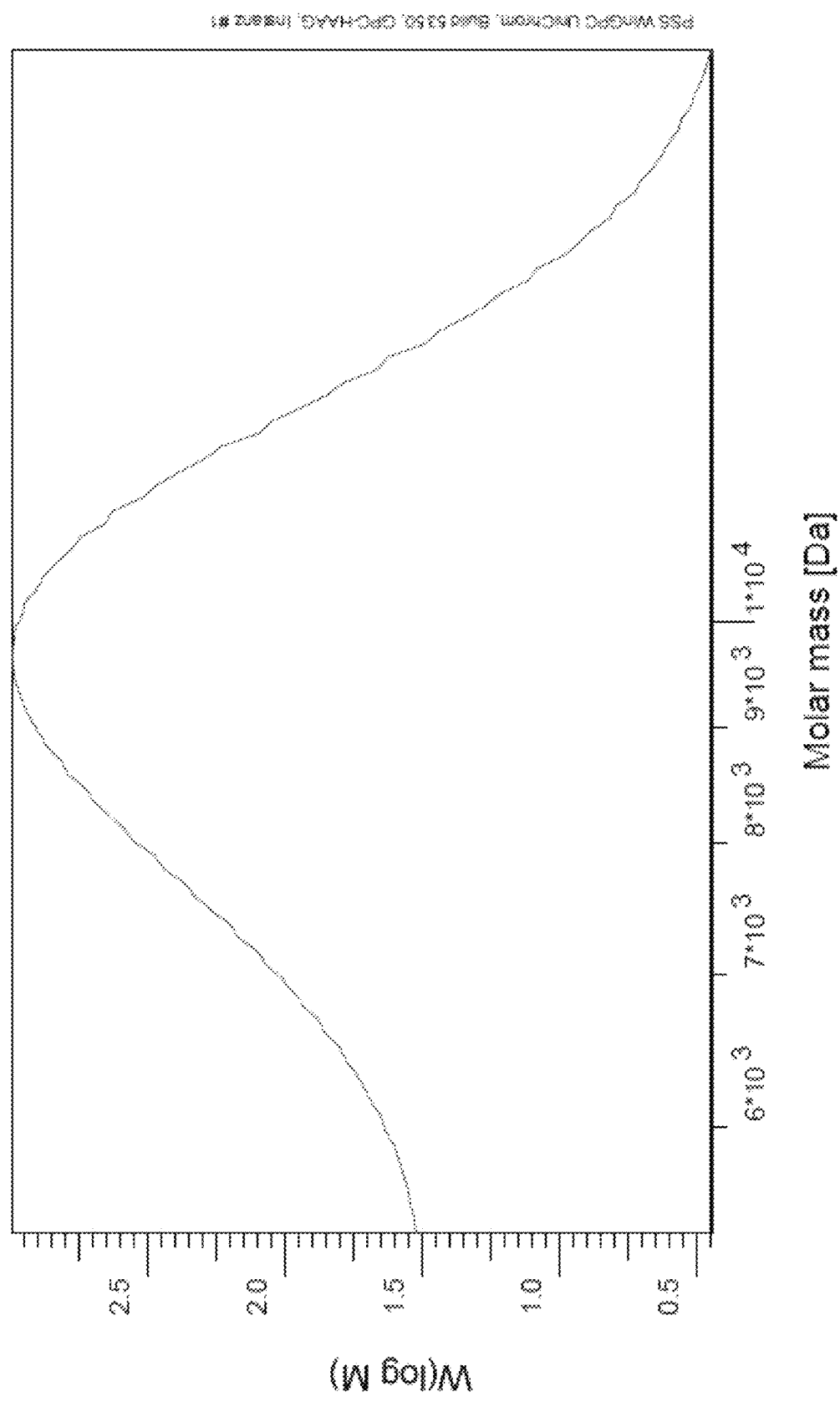
FIG. 18 is a GPC curve of PCPY-cDOX showing monomodal distribution and corresponding table showing molecular mass of PCPY-cDOX at different pH derived from GPC measurements
Figure 19:
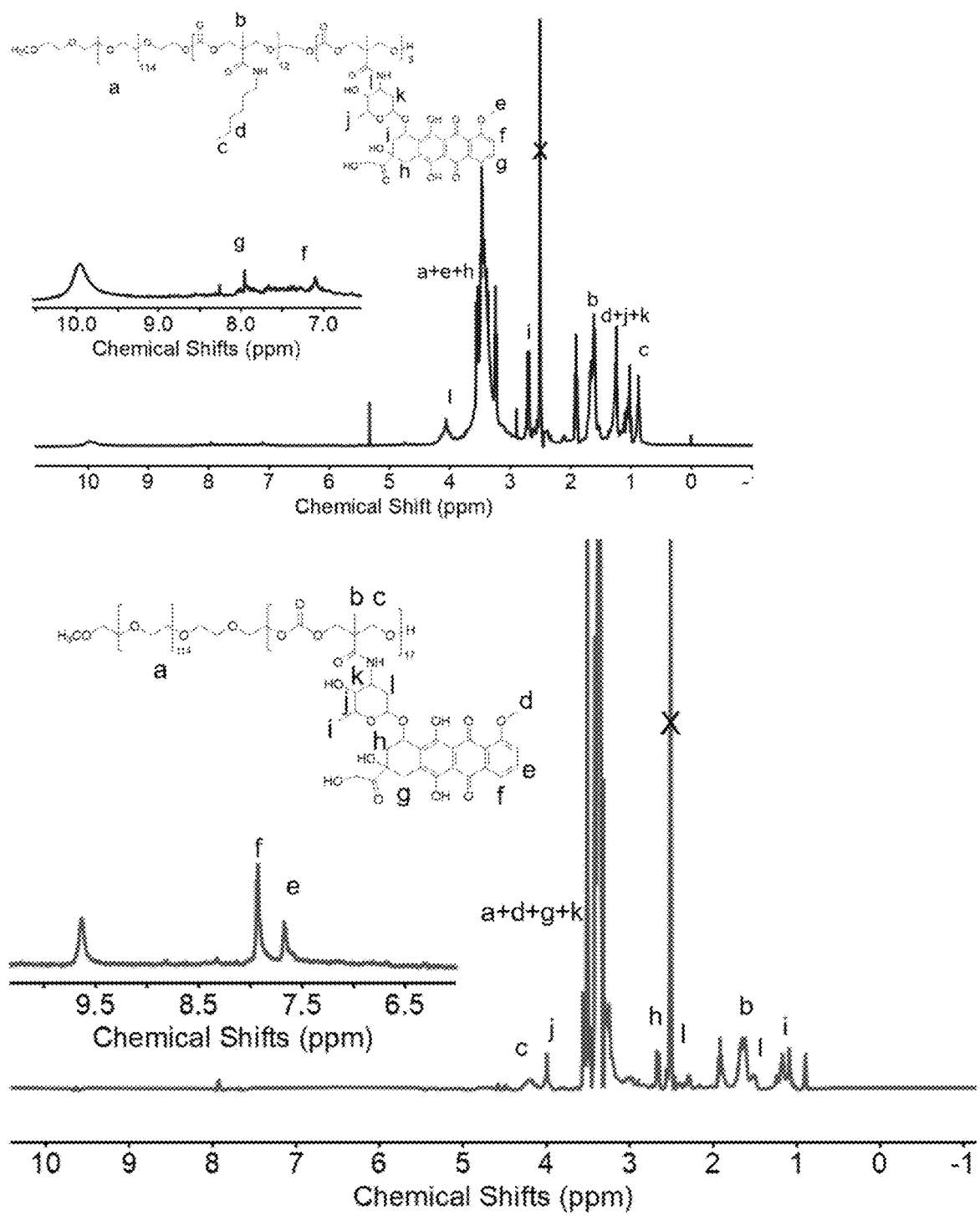
FIG. 19 is a 1H NMR spectrum of pH irresponsive control polymer with hexylamine and doxorubicin (PCHX-cDOX) (blue) and the control polymer with no amine substitution (PC-cDOX) (pink) showing all characteristic peaks of the drug and the respective polymers in d6-DMSO. Small downfield shift of aromatic signals from DOX compared to that presented in FIG. 2 is due to this change of deuterated solvent.

RESULTS: Synthesis and Characterization of the DOX-Conjugated Block Copolymer. NPs typically enter cells through endocytosis, and while contained in the endosomal compartment, they undergo an environmental pH decrease from early to late endosomes and lysosomes The inventors' previous experiments showed the synthesis and characterization of pH-responsive block copolymers, such as those for PCPY (4) and PCDB (5) systems for delivering chemotherapy, that is, gemcitabine, a hedgehog inhibitor (i.e., GDC 0449), or an extracellular receptor kinase-inhibitor (SCH 772984), exclusively for pancreatic cancer. These systems show a pH-dependent conformational switch under low pH conditions to release their therapeutic cargo The inventors' primary focus in this disclosure is to show how molecular connectivity, trigger type, and drug-loading method within NPs differentially affect the toxicity behavior of a loaded chemotherapeutic against cancerous cells and non-cancerous cells, using breast cancer cells and cardiac cells to demonstrate. This is an exciting proposition as the primary chemotherapy of choice for breast cancer, that is, DOX triggers a cardiotoxic effect when administered either via a conventional or NP-assisted route. The inventors designed a set of PEGylated block copolymers of polycarbonates with diversified architectures of pH-sensing side chains, where DOX was loaded either covalently or noncovalently (FIG. 16). First, the inventors prepared a PEGylated polycarbonate variant with covalently conjugated DOX. The inventors selected PCPY as a polymer of choice for synthesizing the polymer-DOX conjugate (FIG. 1, PCPY-cDOX, 6) based on its $pK_a$ value, which causes protonation of the hydrophobic block at the endosomal-lysosomal pH. Nuclear magnetic resonance ($^1$H NMR) and IR spectroscopy were used to characterize PCPY-cDOX (6). As observed from FIG. 2, the —$CH_2$—C—$CH_2$— signals from the hydrophobic arms of PCPY-cDOX were observed at δ 4.3 and 4.5 ppm, while the aromatic signals from DOX were visible at 7.2 and 7.5 ppm, respectively. The characteristic DOX signals were observed in the $^1$H NMR spectrum of PCPY-cDOX constructs at δ 7.2 (br, d, 1H, Ar—H), 7.4 d, (1H, Ar H), 4.1 (br, m, 1H, —OHCH$_2$—CH(O')), and 3.6-3.8 (m, 2H, —OH—CH$_2$—CH (O)R'). The amount of DOX conjugated was estimated using UV-visible spectroscopy. The molecular weight of PCPY-cDOX was analyzed by gel permeation chromatography using water as an eluent. The number-average molecular weight of PCPY-cDOX was found to be 9.6 kDa with a polydispersity index of 1.07, indicating that the conjugate does not contain any free DOX (FIG. 18).

Figure 21:
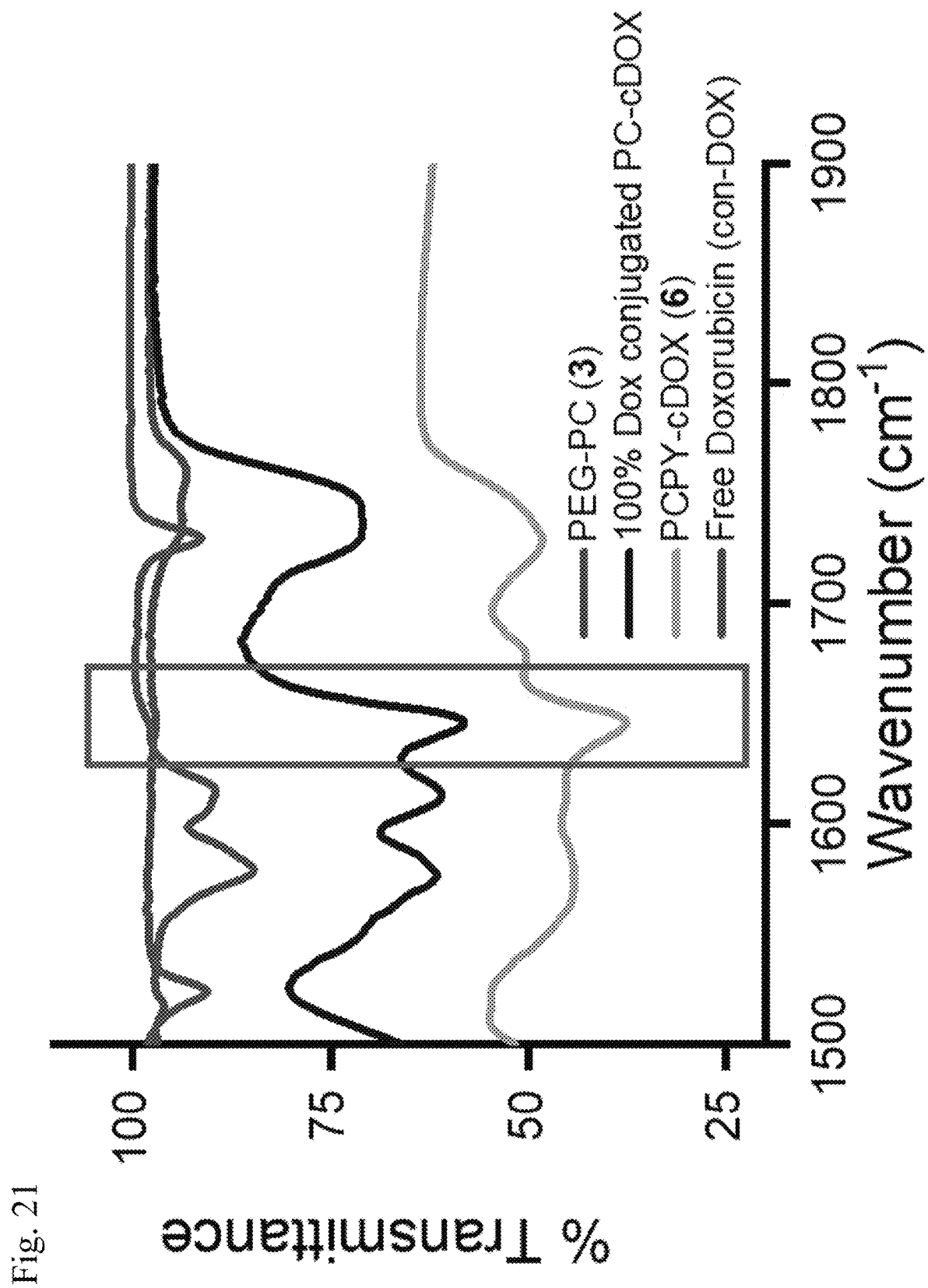
FIG. 21 is an IR spectra of PCPY-cDOX showing the linkage via amide bonding.
Figure 22:
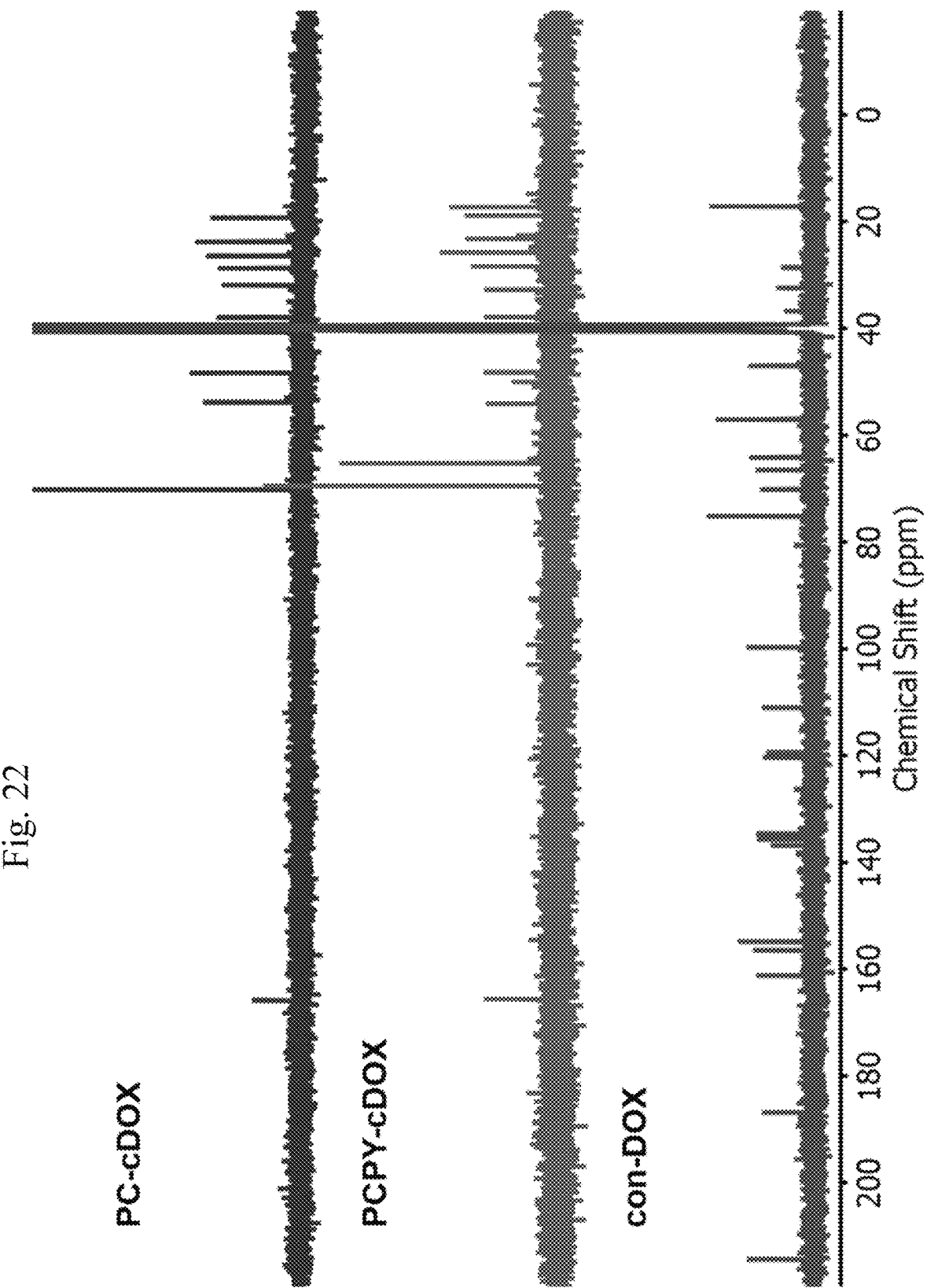
FIG. 22 is a 13C NMR spectra of PC-cDOX (control polymer), Doxorubicin conjugated polymer PCPY-cDOX and free Doxorubicin (con-DOX). The peak at 166 ppm corresponds to the amide linkage which is observed in both the polymers but not in the free drug.

To confirm whether the conjugation of DOX to the PCPY block copolymer was, in fact, mediated through an amide linkage, the inventors prepared several control polymers, where the hydrophobic polycarbonate block was substituted with DOX alone (no tertiary amines, PC-cDOX, 7). IR spectra for these copolymers showed amide stretching signals at 1642 cm$^{-1}$ (FIG. 21). A $^{13}$C spectrum of both the stoichiometrically quantitative DOX conjugated to the PC-cDOX (with no tertiary amine) variant and PCPY-cDOX showed the presence of the amide carbonyl group, which led the inventors to conclude that the conjugation of the drug to the polymer backbone was via O=C—NH bonding (see FIG. 22).

Figure 3A:
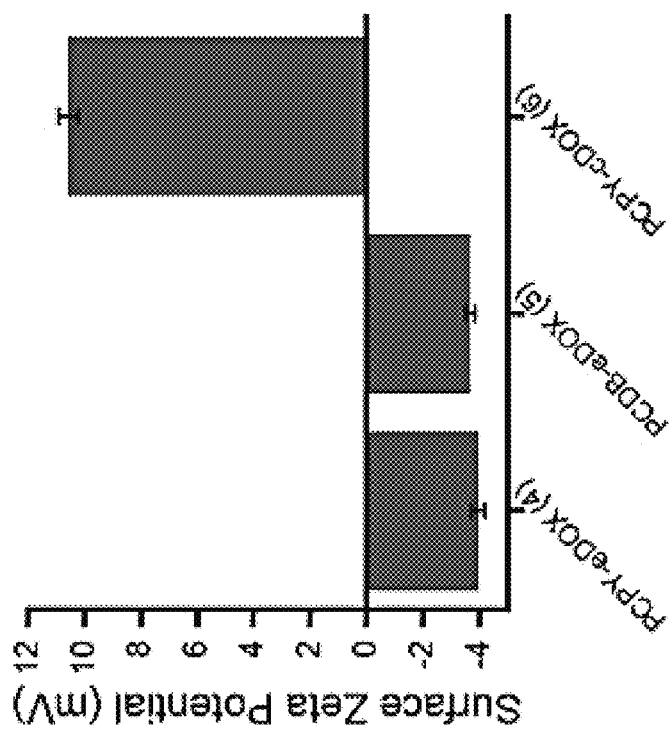
FIGS. 3A-3E show qualities of self-Assembly of Free or DOX-Conjugated Block Copolymers into NPs, where
Figure 3B:
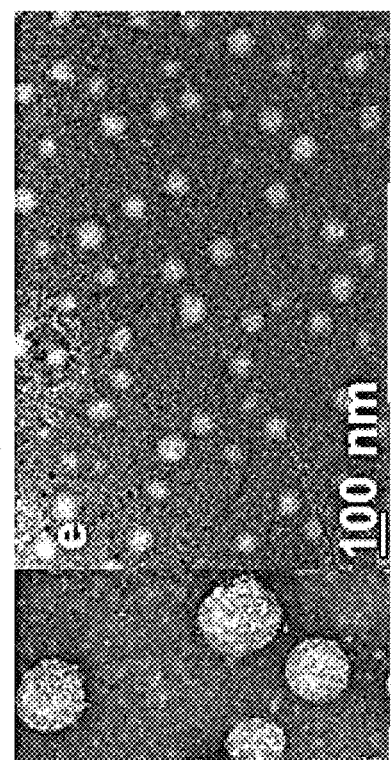
Figures 3C, 3D, 3E:
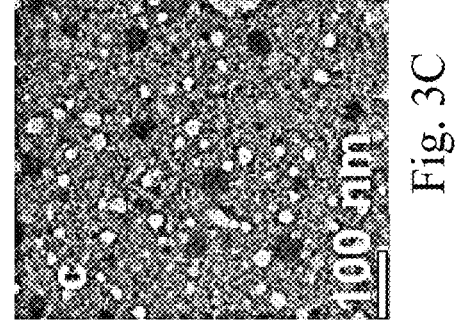

Self-Assembly of Free or DOX-Conjugated Block Copolymers into NPs. The average hydrodynamic diameter of the DOX-loaded PCDB system (5) was found to be 51.02±6.3 nm (n=3), while that from the PCPY system (4) was 106.3±19.3 nm (FIG. 3a). This change in diameter may be attributed to the difference in the structures of the flexible linear amines in the side chains of PCDB (compound 5), as compared to the rigid cycloaliphatic units in PCPY systems (compound 4), which affected their packing parameters. The drug-polymer conjugate (PCPY-cDOX, 6) displayed an average hydrodynamic diameter of 113.5±17.3 nm (n=3). The NPs are formed from local hydrophobic interactions among PC-derived blocks (containing amines, or amine and DOX) shielded by the PEG shell. To the inventors' surprise, the inventors found that the surface charge (zeta potential) of the DOX-loaded PCPY or PCDB nanosystems was anionic (contributed from PEG) with values of −3.96±0.25 and −3.67±0.16 mV for PCPY-eDOX and PCDB-eDOX, respectively, while those derived from PCPY-cDOX exhibited a mildly positive zeta potential of 10.35 mV (FIG. 3b). The surface positive charge might be attributed to π-stacking of DOX inside the NP interior, resulting in polarity shift at the particle surface. The difference in the surface charge may be attributed to the difference in the structures of the tertiary amines, the PCDB system being composed of linear dibutyl amine chains as opposed to the closed pentacyclic structure of the PCPY system. In the case of the drug-conjugated system, the difference in surface charge might be explained by the interactions of aromatic resonance-stabilized structure of DOX and the cationic nature of tertiary amine moieties. TEM of each of these samples showed a distinct population of NPs at pH 7.4, which were of spherical morphology (FIGS. 3c-e). The particles exhibited a smaller diameter when observed through TEM than their hydrodynamic diameter obtained via DLS, most likely due to the shrinkage in the hydrophilic corona, as the samples were dried and subjected to keV beam.

Figure 23:
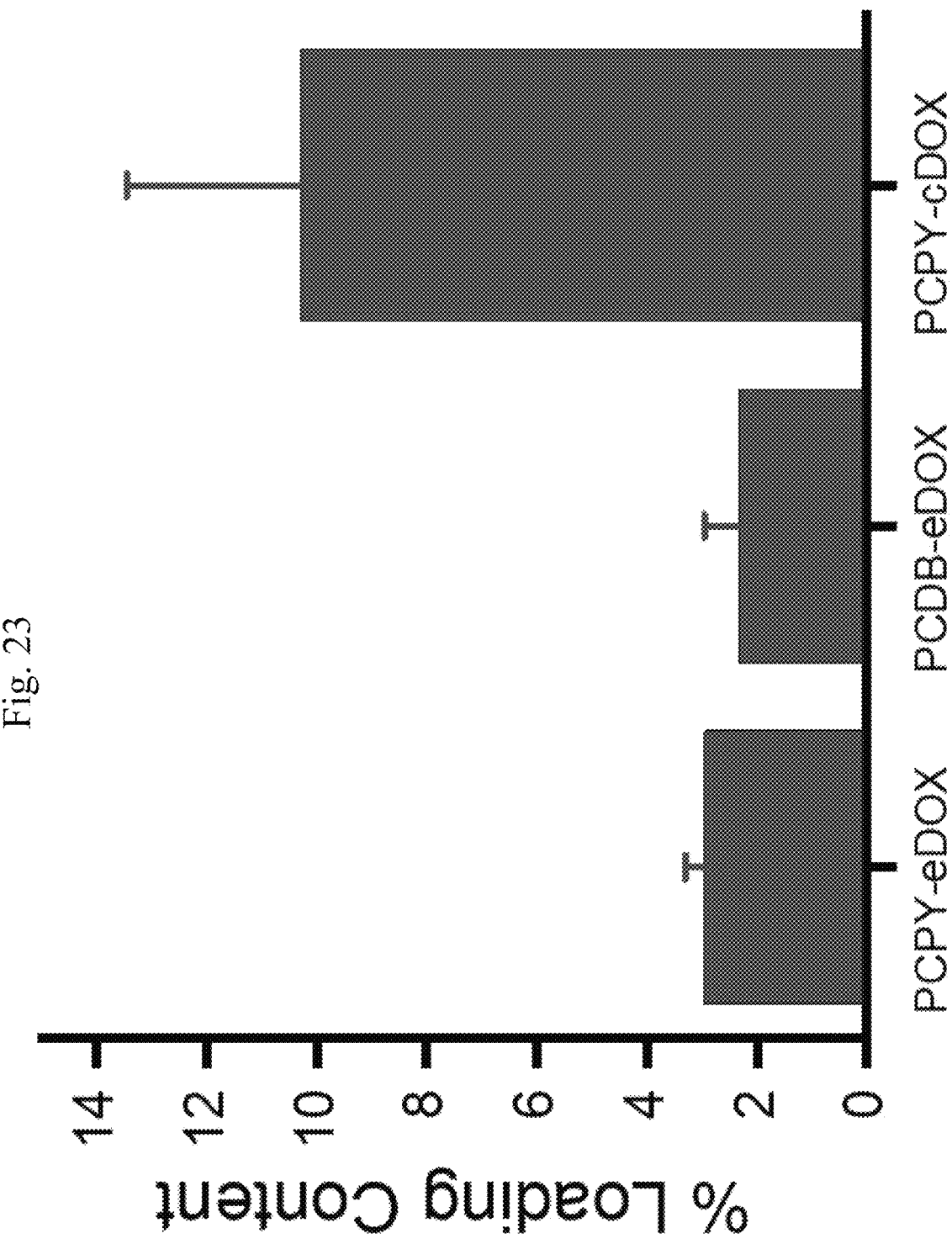
FIG. 23 is a bar diagram showing different loading contents of Doxorubicin in different polymers.

Determination of the Loading Content and Payload of Various Polymeric Constructs. The inventors used the pH-responsive polymers, PCPY (4) and PCDB (5), to encapsulate DOX via noncovalent encapsulation. The inventors also prepared NPs from PCPY-cDOX (6) systems, where DOX was connected to the polymer scaffold covalently via an amide linkage. The loading content of DOX within PCPY and PCDB systems was found to be 2.95 (±0.35) and 2.32 (±0.64) %, respectively. In the conjugated system, that is, PCPY-cDOX, the loading content of DOX had increased at least by ~5-folds than either of the encapsulated systems. In PCPY-cDOX, the DOX payload was found to be ~10.3 (±3.15) % when measured via UV-vis spectroscopy (FIG. 23).

Figure 4A:
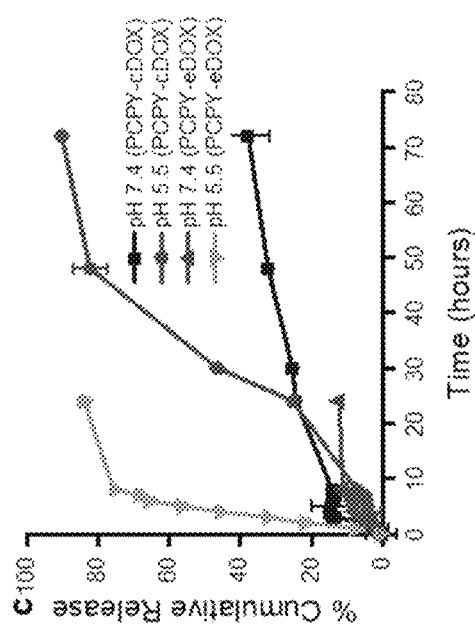
FIGS. 4A-4C are graphs that show Release of encapsulated DOX from (FIG. 4A) PCPY-eDOX (4), (FIG. 4B) PCDB-eDOX (compound 5), and (FIG. 4C) conjugated system (PCPY-cDOX) NPs in the presence of 10% FBS.
Figure 4B:
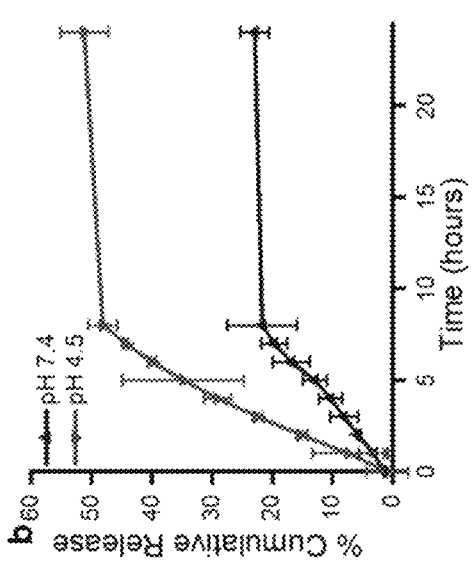
Figure 4C:
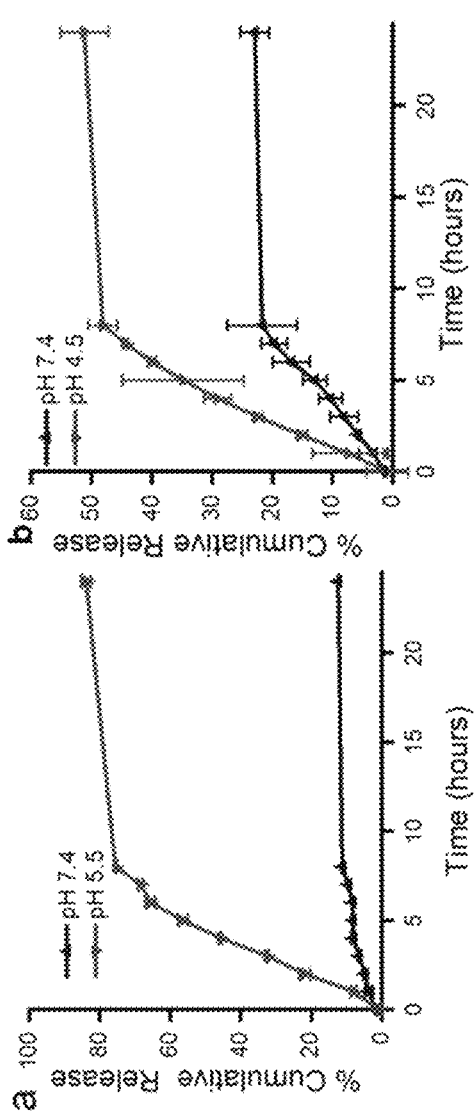
Figure 6:
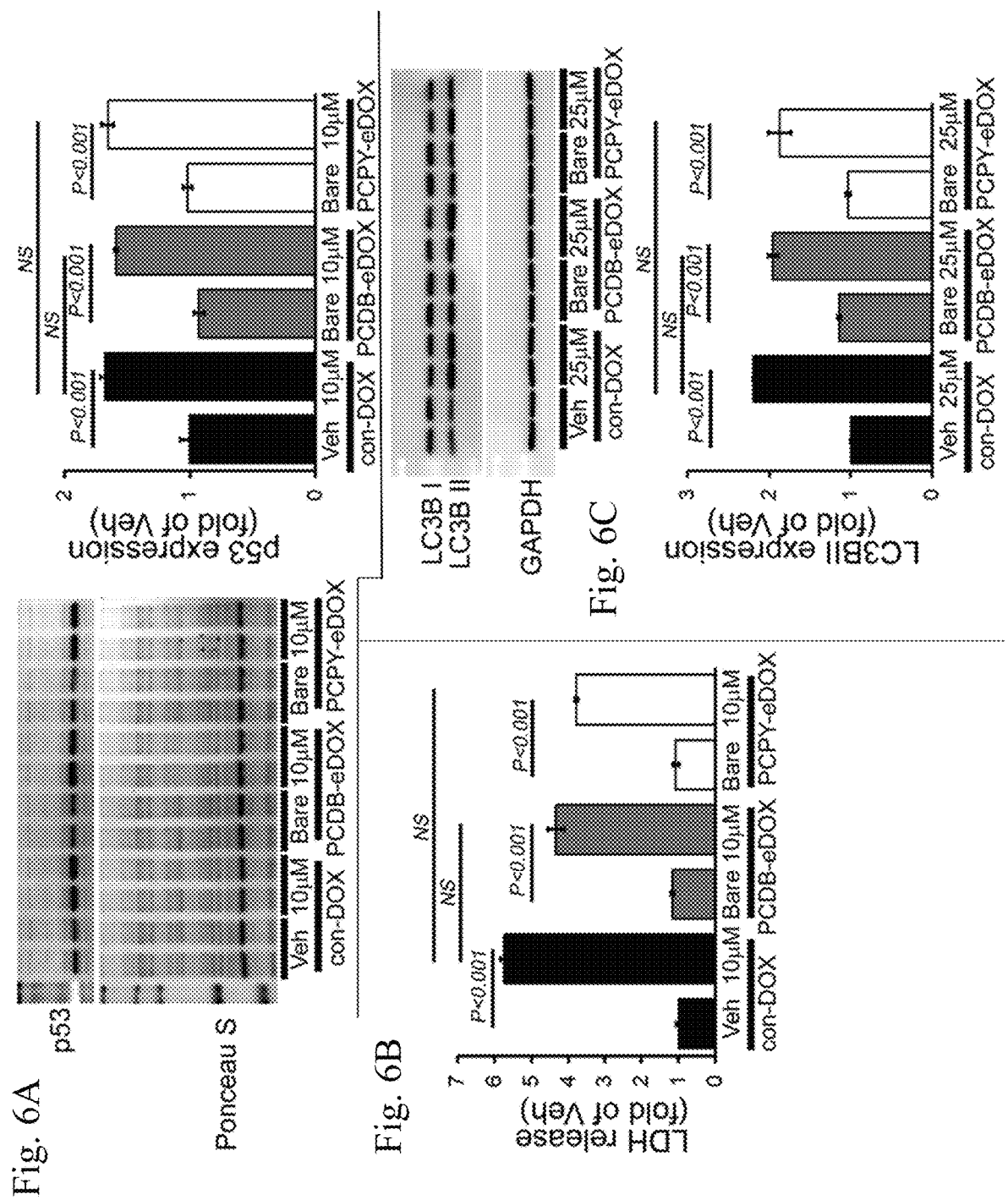
FIGS. 6A-6C show cardiomyocyte toxicity by treatment with con-DOX, PCDB-eDOX, and PCPY-eDOX (10 µM, 24 h) in cardiomyocytes.

Spatiotemporal Release of Encapsulated/Conjugated Drug. The inventors conducted in vitro release experiments with the synthesized carriers under different pH conditions to assess the effect of structural components and DOX-loading techniques on their pH-sensitive DOX-delivery capacity in the presence of 10% FBS. Healthy cardiac myocytes within heart tissues strictly maintain their microenvironmental pH and electrolyte balance, equilibrated at pH 7.4. However, tumor cells, because of their altered metabolic phenotype, decrease the pH of the microenvironment in the extracellular compartment to pH ~6.5.34 Intracellular acidity, which is mostly localized in the early endosome (pH 6.5-5.5) to the late lysosome, can reach as low as 4.5 and is preserved for most types of cells, including cancer cells. To evaluate the comparative effect of dynamically changing pH status within cellular compartments of cancer cells and cardiac cells on the structural diversity of NCs, the inventors encapsulated or covalently conjugated DOX within a structurally different pH-sensitive polycarbonate assembly The inventors' primary objective was to identify how a pH-sensitive polymeric assembly enables drug release into cancer cells and disables drug release into cardiac cells. To understand the effect of encapsulation or conjugation techniques on DOX release from the prepared NCs intracellularly, the inventors carried out DOX dissolution studies from compound PCPY-cDOX (6) in the presence of 10% FBS at pH values 7.4 and 5.5, while for the PCDB system release studies were carried out at pH values of 7.4 and 4.5 due to the lower pK$_a$ of the dibutyl amine side chains. The inventors found out that PCPY-cDOX showed a faster release of DOX at pH 5.5 compared to the physiological pH of 7.4 (FIG. 4a). When comparing with DOX-encapsulated NCs (i.e., PCPY-eDOX and PCDB-eDOX), the inventors found that the drug-polymer conjugate (PCPY-cDOX) displayed a sustained release of DOX with less than 35% release at pH 7.4 at the end of 3 days (FIG. 4b). This observation indicated that PCPY-cDOX systems are more efficient in preventing the release of drug at pH 7.4 and more effective at releasing in acidic pH that usually resides in the tumor microenvironment, as well as in the early endosome. The PCPY-cDOX system, in an acidic environment, released over 80% of its payload at the end of 72 h (FIG. 4c). When compared to an encapsulated system (constructed from polymer 4) with the same polymeric backbone, it was observed that ~80% of the drug was released within 24 h at an acidic pH. This led the inventors to infer that the inventors' approach to conjugate DOX with PC through covalent bonding results in not only a pH-mediated release but also a sustained release of the drug. The inventors observed that the cumulative release of PCPY-eDOX was slightly slower than that of PCPY-cDOX (conjugated system) at pH 7.4. This could be attributed to the difference in surface charge of PCPY-eDOX (negative) and PCPY-cDOX systems (positive), which either hindered or accelerated the diffusion of liberated DOX into the bulk media.

Figure 24:
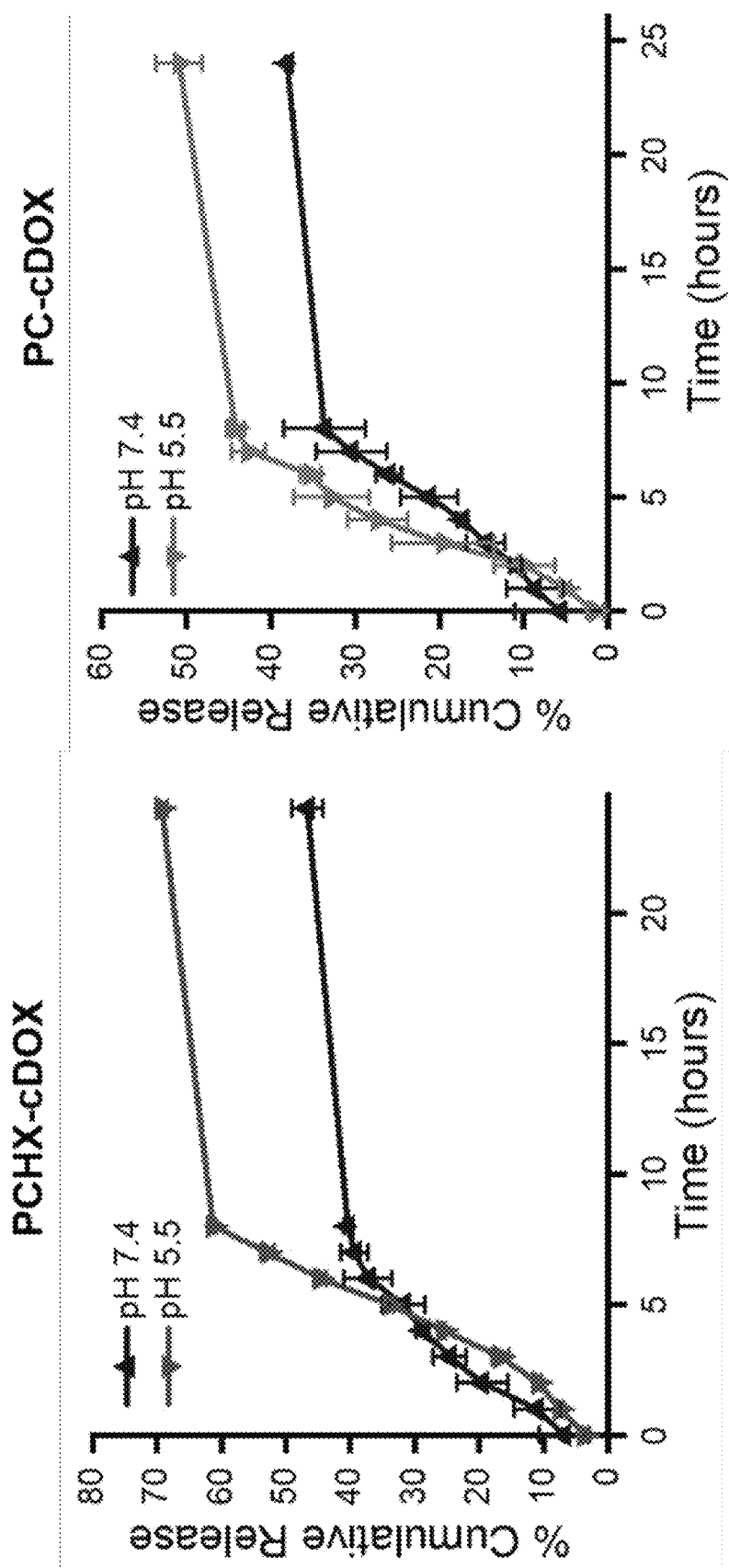
FIG. 24 is release profiles of Doxorubicin from different control polymers at pH 7.4 and pH 5.5.
Figure 25:
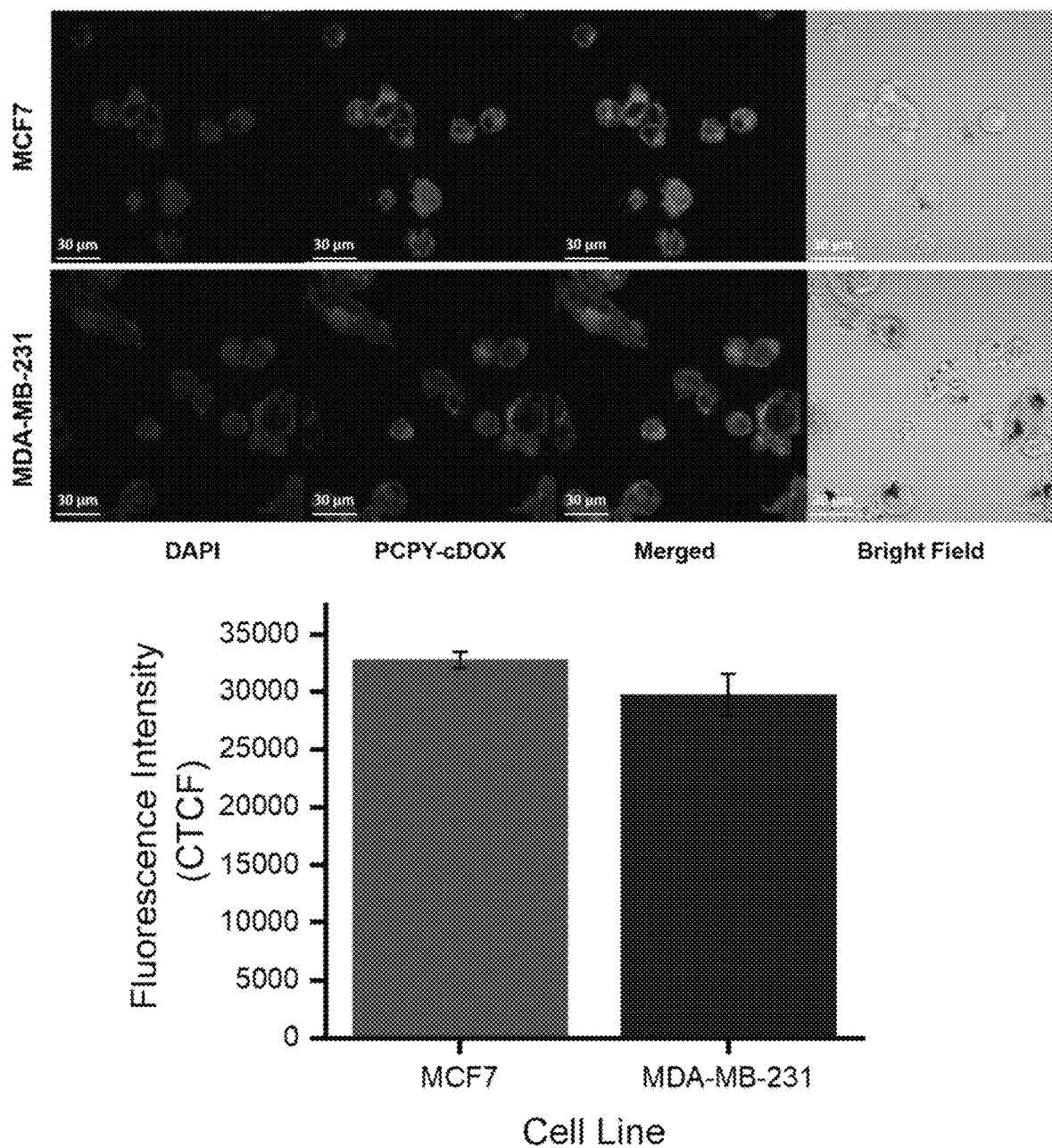
FIG. 25 is Confocal microscopy images of a monolayer culture of (top panel) MCF7 and (bottom panel) MDA-MB-231 treated with PCPY-cDOX for 24 hours showing cell death and leakage of nuclear substances. (Bottom) Corresponding CTCF values).
Figure 26:
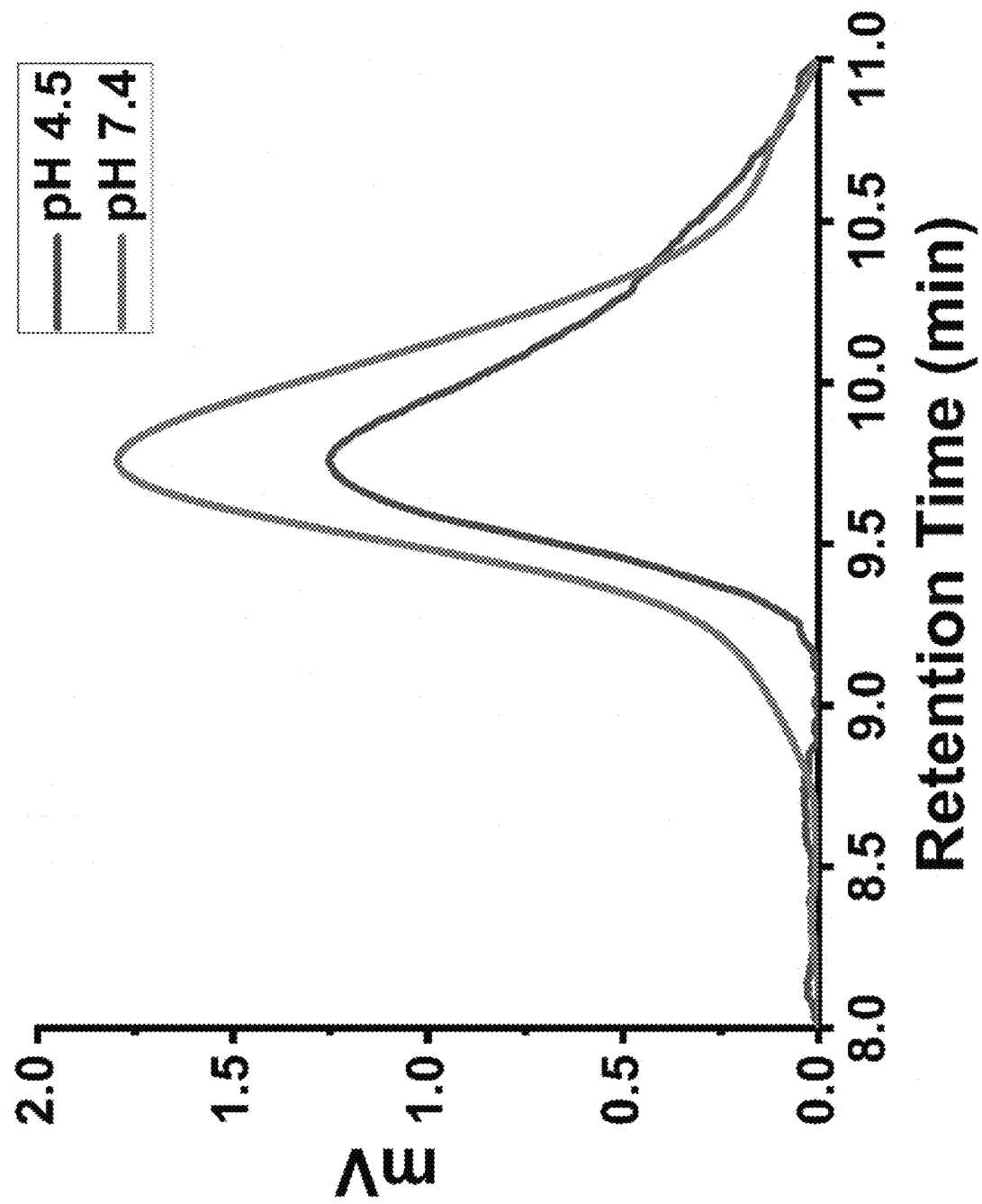
FIG. 26 shows GPC trace of polycarbonate block copolymer at pH 7.4 and 4.5, indicating the polymer backbone does not show significant degradation within the time-frame of drug release (~24 h).

To ascertain whether the pH-based differential release was driven by the pH-responsive units of tertiary amines or an inherent property of the drug itself, the inventors used two control polymers, that is, PC-cDOX (7), which is connected only to DOX and is devoid of any tertiary amines, and another block copolymer, PCHX-cDOX (8). For the latter, the hydrophobic block was decorated with nonpH-responsive amines, such as hexylamines. The inventors conducted release experiments at different pH levels with these block copolymers (FIG. 24). The inventors found that no differential release of DOX was observed in the case of these control polymers at different pH values, which indicated that pH responsivity was driven mostly by the tertiary amine moieties attached to the hydrophobic segment of PCDB and PCPY systems.

Cardiomyocyte Uptake and Cytotoxicity Studies of Encapsulated DOX-NCs. The inventors first set out to identify the cardiotoxic impact of DOX-encapsulated NCs, that is, PCDB-eDOX and PCPY-eDOX systems on cardiomyocytes. To test the effects of encapsulated DOX-loaded NCs directly on cardiomyocytes, the inventors treated NRCs with DOX and vehicle control. In the inventors' earlier studies, the inventors found that conventional DOX-treatment (con-DOX) (1, 5, 10, and 25 µM, 24 h) in NRCs dose-dependently impaired autophagy activity, induced mitochondrial respiratory dysfunction, and altered mitochondrial dynamics, recapitulating the in vivo DOX-cardiomyopathy. Therefore, the inventors treated the NRCs with 10 µM conventional (unencapsulated) formulation of DOX (abbreviated as con-DOX), PCDB-eDOX, and PCPY-eDOX for 24 h. The equivalent concentration of DOX was used for all three treatments and polymeric formulations. The DOX concentration in polymeric formulations was calculated based on drug loading. Bare-PCPY (4) or PCDB (5) was used as negative control (FIG. 5). Confocal fluorescence microscopy images showed that both PCDB-eDOX and PCPY-eDOX released DOX intracellularly, presumably through the endosomal-lysosomal pathway, ultimately causing nuclear localization like that of con-DOX. Immunocytochemistry images of PCPY-eDOX-treated cardiomyocytes showed less nuclear localization of DOX compared to that of PCDB-eDOX (FIG. 5). This is most likely because, under in vitro conditions, the pKa of PCPY side chains is higher than the late endosomal-lysosomal pH, leading to complete ionization of the block copolymer and subsequent destabilization of the PCPY-eDOX construct, thereby leading to DOX release.

On the other hand, as PCDB systems are partially ionized, a reduced amount of DOX was released and translocated to the nucleus because of partial destabilization of PCDB-eDOX NCs. Con-DOX, in its free form, quickly enters the nucleus and intercalates with DNA strands as compared to the drug released from the NCs. This is because free small molecular drugs such as DOX immediately equilibrate between the cell and the nuclear membrane. PCPY-eDOX or PCDB-eDOX requires an additional kinetic step, that is, the release of DOX from the NP membrane, before such equilibration takes place. In fact, such free diffusion is believed by the inventors to be the principal reason for cardiotoxicity with the traditional con-DOX treatment.

We then performed Western blot analysis to observe the p53 protein expression in NRCs, which is the central mediator of molecular events that lead to the development of cardiotoxicity. Both PCDB-eDOX and PCPY-eDOX showed an increased level of p53 protein expression like con-DOX (FIG. 6a). The inventors also observed cellular damage by measuring LDH release in NRCs and found increased LDH release under all the treatment conditions (FIG. 6b). Finally, the inventors measured the LC3B II protein level to monitor autophagy and found significantly increased LC3B II expression indicating impaired autophagy in NRCs (FIG. 6c). These biochemical observations agree with the inventors' confocal fluorescence microscopy-based observations, where PCDB-eDOX and PCPY-eDOX showed nuclear localization similar to con-DOX in inducing cardiotoxicity, thus indicating the relationship between nuclear localization, NP destabilization, and pH-dependent dissociation degree of NP-forming polymers.

Figure 7:
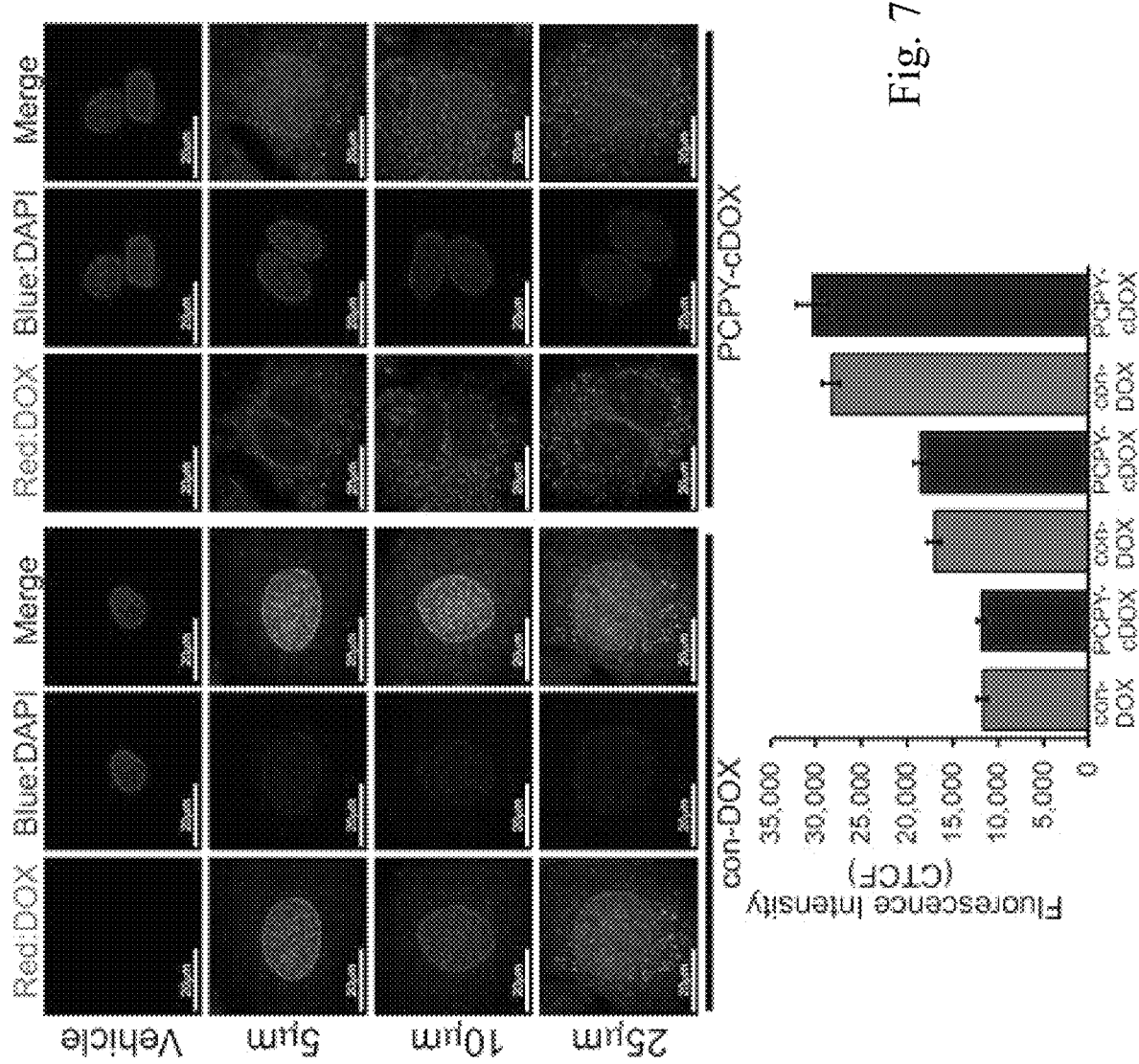
FIG. 7 is confocal fluorescence microscopic images showing DOX distribution in cardiomyocytes in vitro (10 µM, 24 h). Confocal fluorescence microscopic images showing con-DOX and PCPY-cDOX uptake and localization in cardiomyocytes. As shown earlier in FIG. 5, bare-PCPY (no drug) does not show any effect. Bottom panel shows the CTCF data for the image.

Cardiomyocyte Uptake and Cytotoxicity Studies of Conjugated DOX NCs (PCPY-cDOX). As the PCPY-cDOX systems were found to be positively charged, the inventors expected the carriers to be cytotoxic to cancer cells as well as to healthy cells while cardiotoxic to heart cells. Cationic NPs are shown to interact with the negatively charged cell membrane, which promotes nonspecific penetration of the latter inside cells. To validate this hypothesis, the inventors tested the effects of conjugated DOX-loaded NCs directly on cardiomyocytes. The inventors treated primary cardiomyocytes (NRCs) with con-DOX, PCPY-cDOX, and vehicle (FIG. 7). To the inventors' surprise, and in contrast to encapsulated DOX-loaded NCs, PCPY-cDOX at several different doses applied to cardiomyocytes stayed (5, 10, and 25 µM; 24 h) in the cytosol and did not release free DOX, whereas con-DOX completely localized into the nucleus. Cytosolic localization of con-DOX was observed at high doses of DOX (25 µM, 24 h) (FIG. 7). Vehicle and bare-PCPY were used as negative controls.

Figure 8:
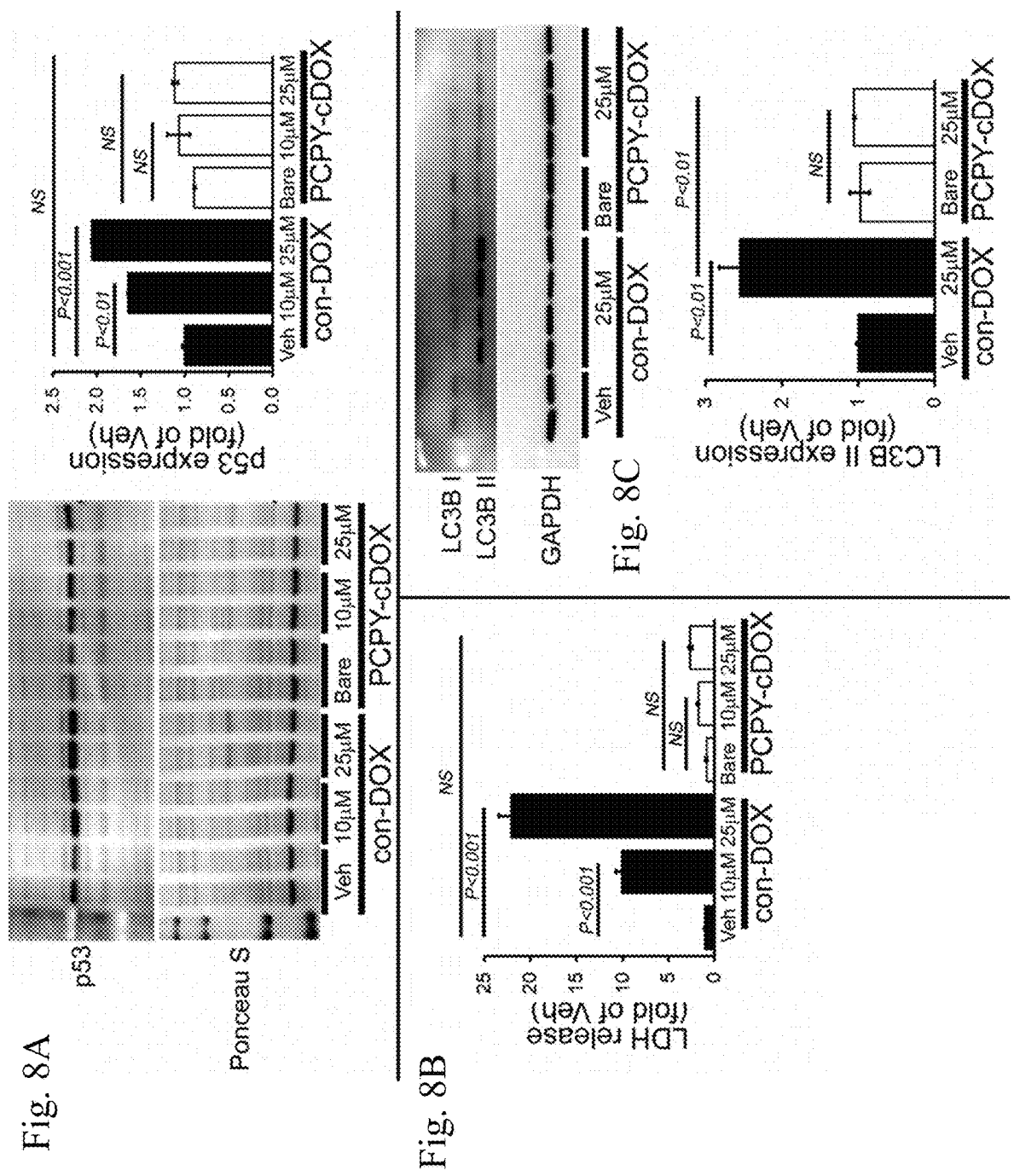
FIGS. 8A-8C show cardiomyocyte toxicity by treatment with con-DOX and PCPY-cDOX (5 µM, 10 µM, and 25 µM; 24 h) in cardiomyocytes.

Next, the inventors performed Western blot analysis to observe the p53 and LC3 protein expression (FIG. 8). Though con-DOX showed a dose-dependent increase in cell death and impairment of autophagy, PCPY-cDOX showed no changes in p53 (FIG. 8a) and LC3II (FIG. 8c) protein expression as well as LDH release in cardiomyocytes (FIG. 8b). Therefore, the inventors' data suggest that treatment with PCPY-cDOX can abrogate the classical cellular toxicity such as cell death and impaired autophagy, as observed with con-DOX.

NPs usually enter cells through endocytosis. Upon cellular internalization, sequential protonation of different domains of NCs along the endosomal-lysosomal pathway is responsible for the diffusion of drugs out of the nanocarrier matrix into the cytosolic space. To examine the effect of pH responsiveness on DOX release within the intracellular environment, the inventors treated cardiomyocytes with DOX-loaded NCs (encapsulated systems derived from PCDB and PCPY and the conjugated system derived from PCPY-cDOX). The inventors investigated the intracellular trafficking of DOX by confocal microscopy using LysoTracker® (FIG. 9). As DOX released from encapsulated NCs (PCDB-eDOX and PCPY-eDOX) showed nuclear localization within 24 h of treatment in cardiomyocytes, the inventors monitored the nanocarrier uptake via the endosomal-lysosomal compartment at an earlier time point (2 h after treatment) where they may release the drug. For this purpose, the inventors used LysoTracker®, which is a small, membrane-permeable dye that nonspecifically labels mild to strong acidic membranous structures such as lysosomes, endosomes, phagosomes, and autophagosomes. After 2 h of incubation with DOX-loaded NCs, the encapsulated DOX-loaded NCs (PCDB-eDOX and PCPY-eDOX) showed uptake and localization in endosomes-lysosomes on cardiomyocytes as well as the DOX released from these NCs was found to localize to the nucleus (FIG. 9). All the con-DOX was found mostly to localize in the nucleus and some in the cytosol.

Interestingly, the conjugated DOX-loaded NCs (PCPY-cDOX) localized into the cytosol with very little accumulation in the endosomes-lysosomes and was not found in the nucleus. These data suggested that pH-responsive encapsulated DOX-loaded NCs were disrupted by the lysosomal pH drop where DOX was released and subsequently diffused into the nucleus where it could bind to the DNA. However, the conjugated DOX-loaded NCs (PCPY-cDOX, 6), because of their mild cationic charge, engaged negatively charged cell membranes to gain cellular internalization escaping the endocytosis and subsequent endo-lysosomal transport. Therefore, the conditionally unstable amide bond remained intact, and the nanocarrier did not release any DOX from the NCs rendering it devoid of the cardiomyocyte toxicity. The pH sensitive motif, that is, for example, a tertiary amine trigger, is extremely beneficial in these structures to initiate drug release into the tumor microenvironment and not in off-target regions that are highly buffered (such as cardiac tissues). The inventors explain the fact that PCPY-cDOX enters into the cytosol of cardiac myocytes in its intact form because the cardiac microenvironment is not acidic. As a result, the conjugated system escapes the endosomal-lysosomal pathway to activate drug release. On the other hand, in the tumor microenvironment, DOX is cleaved off from this system as a function of tumor pH, which is acidic, thereby showing substantial toxicity to cancer cells.

Figures 10A, 10B:
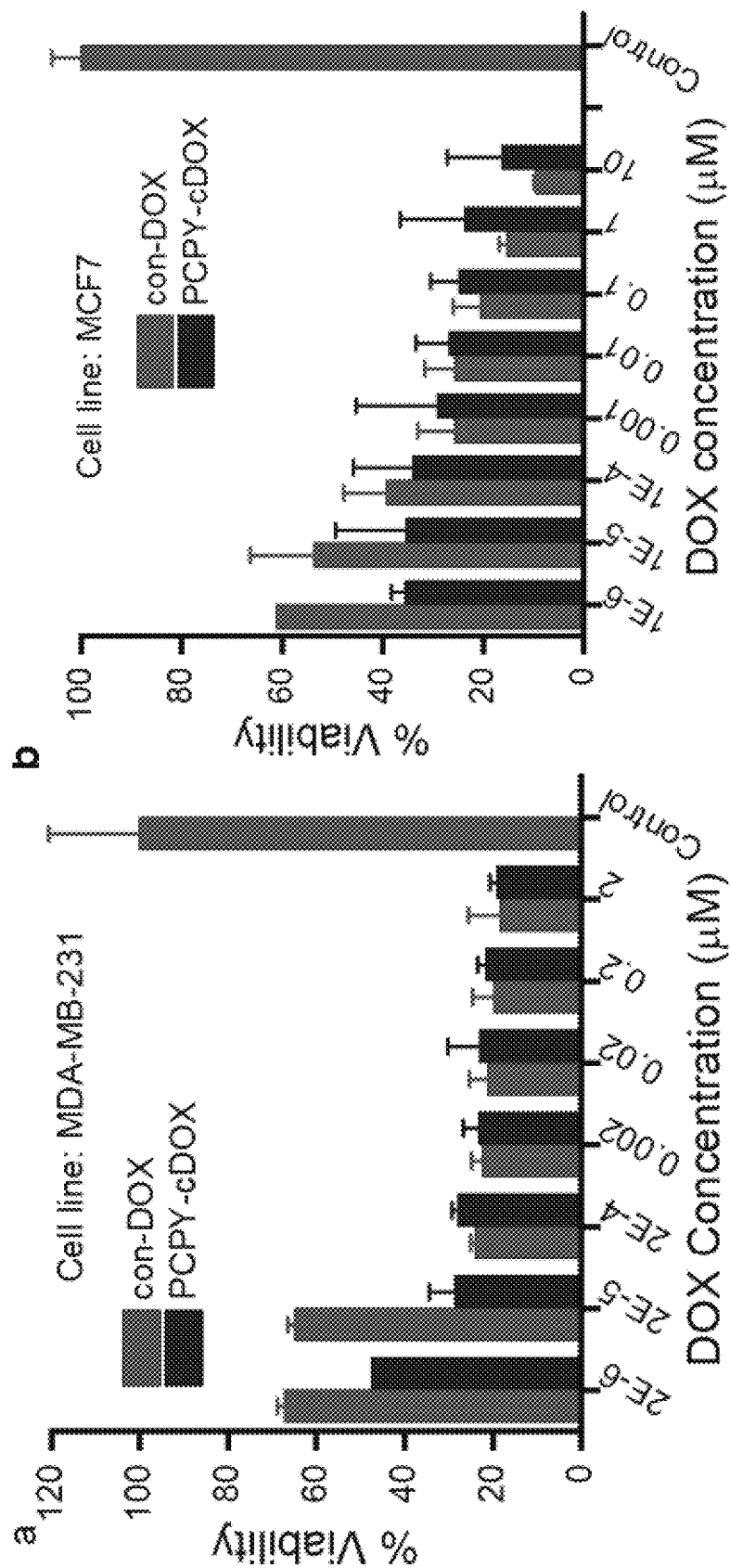
FIGS. 10A and 10B are two graphs showing Cell viability of drug-bound NPs derived from PCPY-cDOX and con-DOX (free DOX) on (FIG. 10A) MDA-MB-231 cells and (FIG. 10B) MCF7 cells (n=3).

Cancer Cell Uptake and Cytotoxicity Studies of Conjugated DOX-NCs (PCPY-cDOX Systems). As PCPY-cDOX (6) showed an extended release of DOX under cell-free acidic microenvironment conditions and the encapsulated systems showed increased cardiotoxicity, for in vitro validation, we, therefore, set out to investigate the effect of PCPY-cDOX on the proliferation of a triple-negative breast cancer (TNBC) cell line, that is, MDA-MB-231 and an ER+ cell line, that is, MCF7 using the MTS assay. The inventors observed that at equivalent concentrations of DOX, PCPY-cDOX showed higher cell mortality (drug dose varied from 2 to 2×10−6 µM) compared to the free drug (FIG. 10). The higher cytotoxic effect may be attributed to a slower rate of release of DOX from the conjugated system even at the endosomal-lysosomal pH. The inventors' have shown that the inherent nontoxicity of the polymer itself is up to 10 mg/mL.

To study the cellular uptake and internalization of the NCs derived from

Figure 11B:
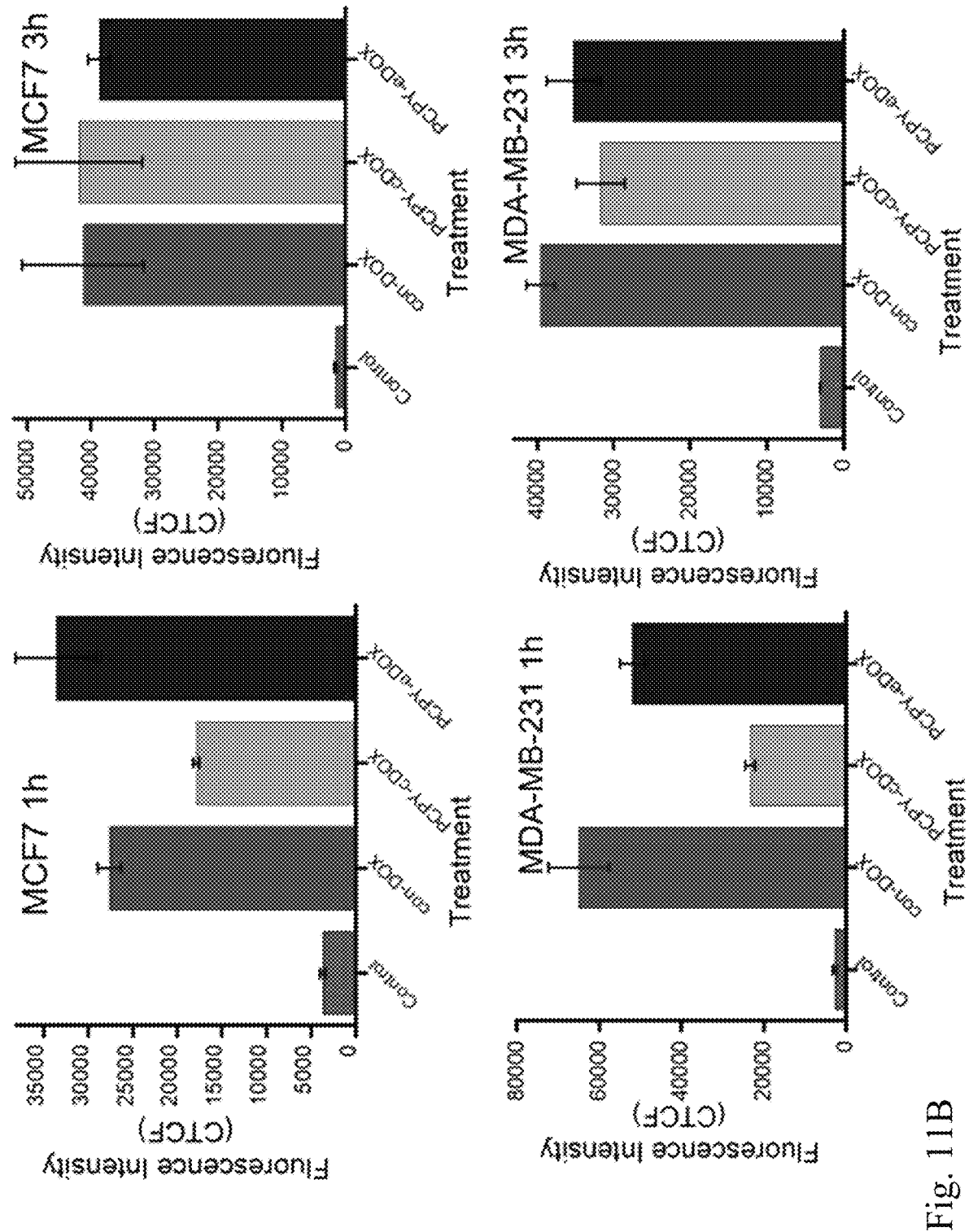
FIG. 11b shows the corresponding CTCF analysis for the images.

PCPY-cDOX, the inventors used monolayer cultures of MCF7 and MDA-MB-231 cells incubated with the nanocarrier suspension for different time points, that is, 1 and 3 h. The cells were imaged using confocal fluorescence microscopy postincubation. The inventors observed a time-dependent uptake of NCs for both the cell lines (FIG. 11). The inventors also observed drug-mediated cytotoxicity in breast cancer cells when they were exposed to PCPY-cDOX systems. Because of the mild surface cationic charge, it is not unlikely that these NCs might bypass the endocytotic pathway and activate in the low pH microenvironment of early and late endosomes. In such an event, the inventors envision that the observed cytotoxicity for PCPY-cDOX might be due to the drug release from PCPY-cDOX under generalized microenvironmental acidification brought about by highly glycolytic variants of cancer cells. Subsequently, released DOX reached into the nucleus and induced cell mortality, causing leakage of the nuclear substances into the cytoplasm (see FIG. 25).

Figure 12:
FIG. 12 is spheroid cultures of (top panel) MDA-MB-231 cells and (bottom panel) MCF7 cells showing the internalization of drugconjugated NCs derived from PCPY-cDOX.
Figure 13:
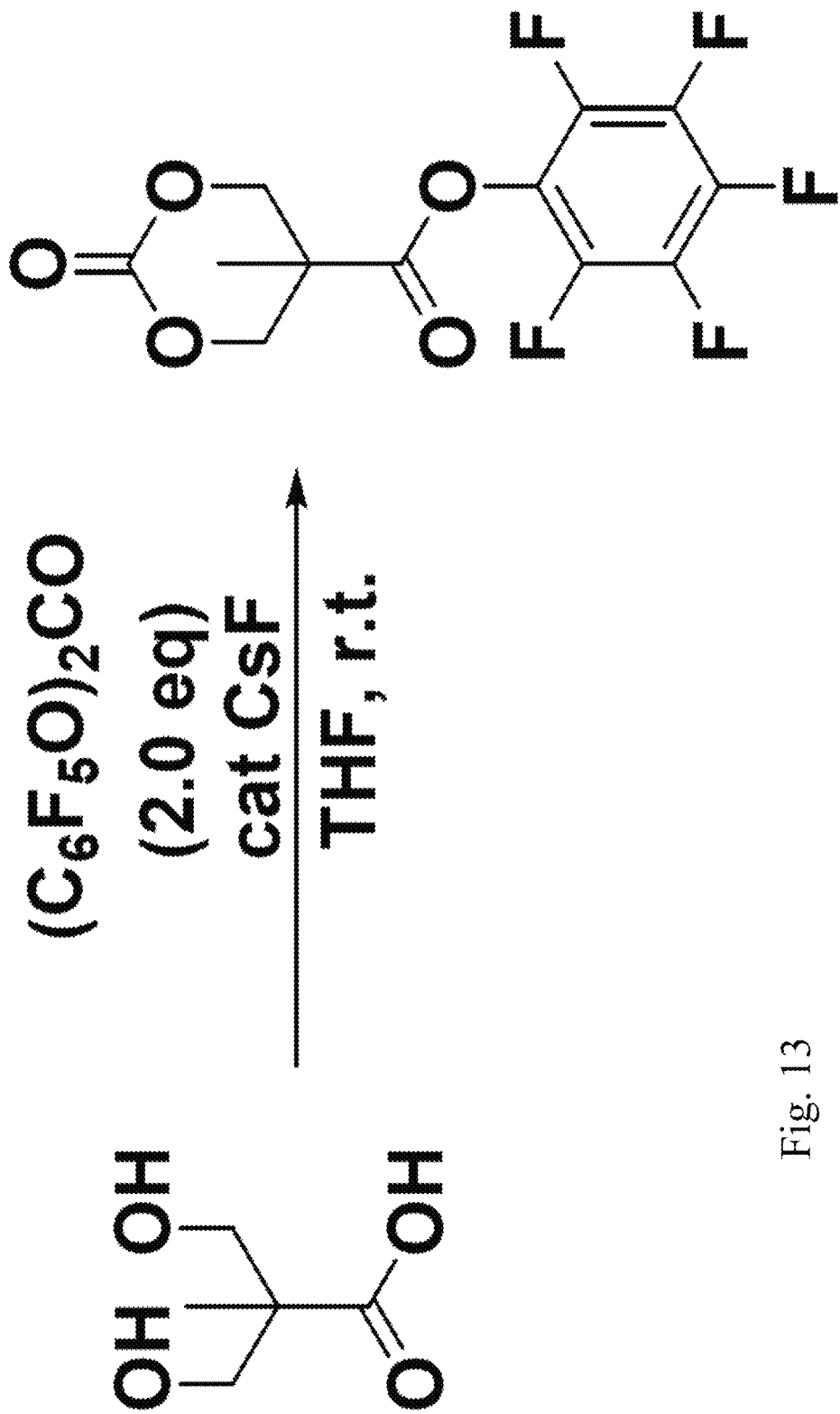
FIG. 13 is a schematic of a synthetic route of the pentafluorophenyl protected bis (methoxy propionic acid) derivative.
Figure 14:
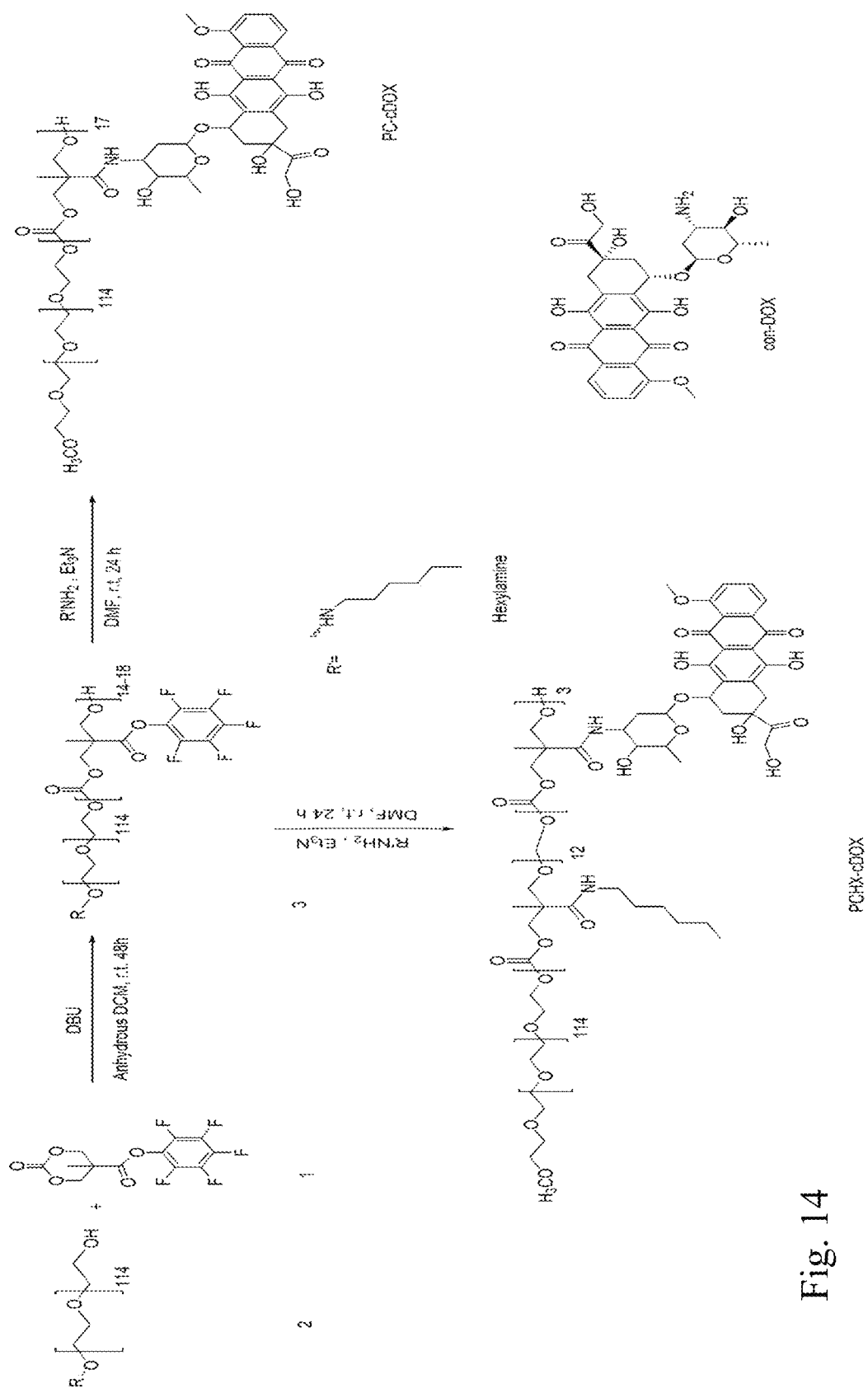
FIG. 14 is a schematic for a synthetic scheme for control polymers PCHX-cDOX and PC-cDOX. In order to ascertain the linkage via which the doxorubicin is conjugated to the inventors' pH responsive system is indeed via an amide bond, the inventors synthesized a compound where the inventors attempted to replace all the pentafluorophenyl esters using doxorubicin only without any amines. A second control polymer to determine the effectiveness of the pH responsive system on the release of DOX was also used. For this the inventors used a pH irresponsive amine (hexylamine) with Doxorubicin and conjugated them to the starting polycarbonate (FIG. 14 compound 3) The control polymers PC-cDOX and PCHX-cDOX were synthesized as follows: 30 mg (0.006 mmol) of mPEG-OH (FIG. 14 compound 2) and 100 mg (0.3 mmol) of the monomer (FIG. 14 compound 1), were dissolved in 3 mL anhydrous DCM under nitrogen and DBU (10.19 mg, 0.06 mmol) was added to the solution to facilitate polymerization. After stirring for 48 h at room temperature, the reaction was quenched by precipitating into diethyl ether and centrifuging at 7000 rpm for 30 minutes. The supernatant was decanted, and an equal volume of diethyl ether added and the solution re-centrifuged for another 30 minutes at the same speed to yield the polycarbonate block (FIG. 14 compound 3). The synthesized intermediate block copolymer, polycarbonate (FIG. 14 compound 3) was aminated with hexylamine to generate PCHX-cDOX and con-DOX to generate PEG-PC-cDOX respectively, in the presence of triethylamine in DMF at room temperature for 24 h. The polymers were purified by precipitation in cold ether.

To investigate whether PCPY-cDOX could penetrate through the 3D tumor microenvironment to transport therapeutic concentrations of DOX intracellularly, the inventors established spheroid cultures of MDA-MB-231 and MCF7 cells, which were treated then with DOX-loaded NCs (PCPY-cDOX). As shown in FIG. 12, the inventors observed the presence of DOX in the spheroid microenvironment of both cell lines, indicating the diffusion of NCs loaded with drug inside the tumor tissue. In the absence of any targeting ligand as that of the inventors' system, such level of penetration is mostly due to the mild, surface cationic charge of the polymer assembly.

The nanocarrier formulation of DOX, such as Doxil, where the drug has been encapsulated within a liposomal system, has shown enhanced accumulation of the drug in the tumor microenvironment, mostly mediated by the enhanced permeation and retention (EPR) effect. However, liposomal constructs suffer from several fundamental disadvantages such as a drug carrier in terms of systemic stability and premature release of the encapsulated content. Although cardiac toxicities have been extensively controlled when using liposomal DOX formulation, compared to the free drug, it is not entirely abrogated. Dose-limiting toxicity is still an issue for both liposomal and conventional DOX formulations. Besides, CARPA and hand-and-foot syndrome is also a set of toxicities associated with Doxil infusion. To enhance control over drug release from the delivery systems, more stable polymeric NCs and drug conjugates have been developed for DOX, a few of which are in clinical trials. Preclinical studies almost exclusively showed reduced accumulation of NCs (with or without DOX) in cardiac tissues. Tumor heterogeneity is a significant problem that does not necessarily guarantee the success of nanotherapy that solely depends on the EPR effect. Hence, to gain additional control over tumor accumulation, engineered NPs, particularly, those with environment-responsive modalities, have been designed, which substantially improve targeted activation and accumulation of the drug payload only in a tumor-cell specific manner. These systems act by exhibiting structural or conformational changes in the carrier-forming macromolecular units in response to a cellular or an extracellular stimulus of chemical, biochemical, or physical origin. These stimuli result in the release of drugs only within a specific pathological environment, sparing other physiological compartments from the adverse effects of the drug. Several solid tumors such as TNBC and pancreatic cancer cells show the Warburg effect, leading to the microenvironmental acidification associated with tumor hypoxia. Therefore, an exclusive pathological signature is set across the tumor tissue that can be harnessed for localized delivery of a chemotherapeutic payload released from pH-sensitive NCs. Although a vast arsenal of such nanosystems, either polymeric, liposomal, or micellar origin, have been reported following such delivery strategy, the fate and mechanism of DOX-loaded, stimuli-responsive carriers in cardiac myocytes have not been systematically explored. Therefore, the inventors' broader objective in this work was to systematically identify how the carrier architecture and how DOX is associated with the carrier affect the disposition of the drug within cardiac myocytes, so this therapeutic method could be applied to other anti-cancer drugs for use against other cancer cells with an acidic microenvironment.

First, the inventors screened two types of pH-sensing carrier candidates, that is, block copolymers which sense pH drop that persists across the extracellular compartment of tumor tissues (pH 6.5-5.5, PCPY systems) and those which register the intracellular pH status that exists across the endosomal-lysosomal compartment (pH 5.5-pH 4.5, PCDB-systems). In both systems, DOX was physically encapsulated within the carriers (PCPY-eDOX and PCDB-eDOX) in the form of NPs. As noncovalent encapsulation, in many instances, yields suboptimal drug loading and burst release, the inventors also designed a pH-responsive, chemically conjugated DOX carrier using a PCPY motif, leading to PCPY-cDOX systems. In these constructs, DOX was conjugated through a "conditionally unstable amide" linkage within a tertiary amine. To design these conjugates, the inventors have devised a facile route to chemically attach DOX with the amphiphilic polymer backbone. The inventors observed that such a conjugation technique not only improved DOX loading within the nanocarrier and rendered the construct sensitive to extra-/intracellular pH drop but also controlled DOX release in a pH-sensitive pattern.

Figure 15:
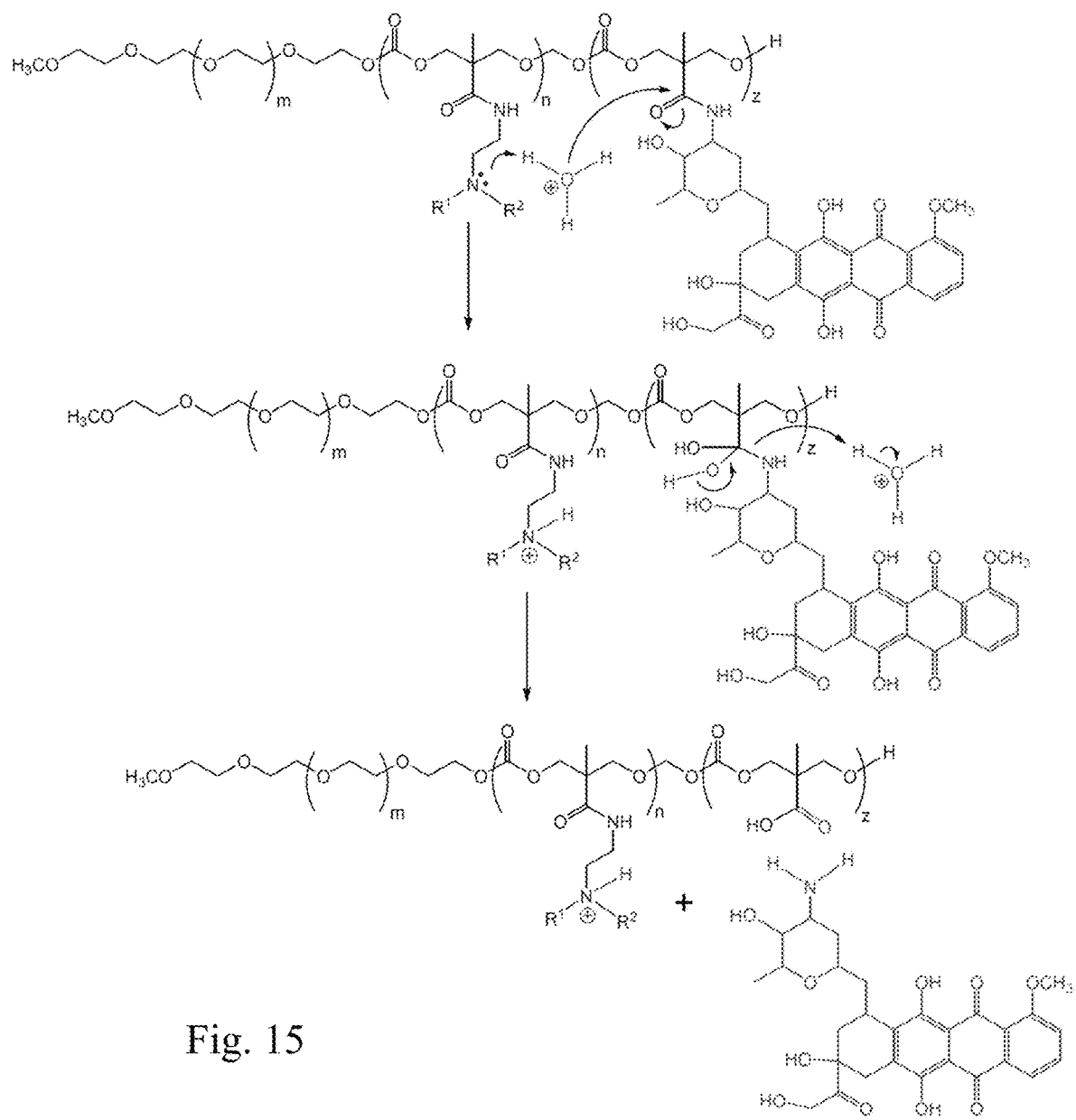
FIG. 15 is a schematic of a step-wise mechanism for the release of DOX from PCPY-cDOX systems.

Mechanistically, the inventors hypothesize that the presence of carbonyl carbon of the amide group in the vicinity of the tertiary amine will decrease the local pH of the molecular microenvironment of the carbonyl carbon, driving the liberation of DOX from the polymer scaffold (FIG. 15). Thus, a parallel hypothesis of this work was to prove which type of DOX encapsulation technique, that is, covalent or non-covalent, shows a higher influence on cardiac myocytes in terms of their cellular and biochemical functions. For this reason, the inventors designed two types of nanocarrier architectures of DOX, intending to tease out the cellular pathways through which DOX-conjugated or DOX-encapsulated systems trigger cardiotoxicity, thus allowing application of this method to other chemotherapeutics for other cancers and preventing toxicity to other non-cancer cells.

In the present study, the inventors used cultured primary cardiomyocytes to study the cardiotoxicity of DOX. In other studies, using neonatal cardiomyocytes, the inventors recapitulated and established the cellular toxicity associated with DOX. The studies showed an impairment of the autophagic degradation process and mitochondrial dysfunction. Therefore, the inventors considered cardiomyocytes for this study and determined the toxicity of both encapsulated and conjugated DOX-loaded NCs. The inventors also monitored their subcellular localization, cytotoxicity, and effect on cellular signaling. The inventors observed that the noncovalently encapsulated DOX-NCs showed a similar level of nuclear localization, as observed with free DOX, suggesting premature drug release from the NCs within the endosomal-lysosomal pathways for these systems in cardiomyocytes.

In contrast, covalently conjugated DOX-loaded NCs (PCPY-cDOX) at several different doses applied to cardiomyocytes did not release free DOX from the NCs and escaped the lysosomal localization. In addition to conjugation chemistry, where DOX is connected to the polymer backbone through amide coupling, the surface charge of these carriers (10.35 mV) is the most likely driver for these observations. Important to note is that despite the cationic surface charge, these NCs did not show adverse effects on cardiomyocyte viability; however, they were found to have detrimental effects on cancer cells. These studies provide an effective way to kill cancer cells without affecting the cardiac cells, evidencing the effectiveness of this discovery, and the applicability on preventing toxicity to other non-cancer cells, as well as the applicability of loading other chemotherapeutics on the PCPY and/or using the covalently conjugated chemotherapeutic-loaded NCs on other cancers. Our drug-release studies showed that enhanced DOX release from the NPs occurs at pH 5.5 or below compared to the release at pH 7.4 (FIG. 4). The inventors attempted to explain this disparity mechanistically in terms of pKa values for the two amines used in PCPY and PCDB systems. These amines are 2-pyrrolidine-1-yl-ethyl-amine, PY, and N,N'-dibutylethylenediamine, DB, with pKa values of 5.4 and 4.0, respectively. Therefore, at pH 5.5, while 44% of PY will be protonated, only 3% of DB groups will have protonation. At pH 4.5, 89% of PY and 24% of DB will be protonated. Accordingly, the inventors observed a more pronounced DOX release from the PCPY NPs than from the PCDB counterparts at pH 5.5 and 4.5. As the pKa of DB is less than that of PY, a more reduced pH (4.5 compared to 5.5 for PY, see FIGS. 4a-b) is required to achieve a substantial amount of DOX release from these NPs. Based on these observations, the inventors propose a possible DOX release mechanism under a reduced pH involving general acid-catalysis, as presented in the FIG. 15. The inventors also showed that within the timeframe of studies, the polycarbonate backbone does not reduce the average molecular weight (FIG. 26) at pH 7.4 or at <5.0, indicating that such acid-catalyzed hydrolysis of DOX is the prevalent mechanism of degradation that causes main chain breakdown. Of note, this mechanism appears valid only for an acidic microenvironment, such as is present in the tumor microenvironment or within the endo-lysosomal pathways.

CONCLUSIONS: In conclusion, the inventors present here that DOX-conjugated pH-responsive PEG-b-PC copolymers (PEG-PC) abrogates cardiotoxicity without compromising the anticancer efficacy of DOX. Moreover, the inventors also demonstrated that drug molecules, when physically encapsulated inside PEG-PC NCs, show a premature release of the drug into the cytosol of cardiomyocytes. Analogous to earlier work with different cell lines, the inventors also observed that encapsulated DOX-NCs initially localized within the late endosome-lysosome of cardiomyocytes, with subsequent release of free DOX in response to the acidic pH of the lysosome. The free DOX ultimately diffuses via the cytoplasm into the cell nuclei. The results obtained from this study indicated that the encapsulated DOX-NCs were most likely being taken up by cardiomyocytes via the endocytic pathway and showed pH-sensitive drug release.

Interestingly, the conjugated DOX-NCs had a higher drug loading capacity, mildly positive zeta potential, and displayed a higher level of bioavailability, all of which led to a lack of cardiomyocyte toxicity triggered by this system, as free DOX was not released in the late endosome-lysosome compartment of cardiomyocytes. From these results, the DOX-conjugated pH-responsive PEG-PC block copolymers appear to be effective chemotherapy with an enhanced therapeutic efficacy devoid of cardiomyocyte toxicity for cancer cells.

Based on the inventors' discovery, the inventors can attach at least any cancer treatment drug or anticancer pharmaceutical which has a primary ($1°$) amine ($-NH_2$) group in within their structure. Such attachment can be carried out either covalently (by forming bonds) or non-covalently (via electrostatic or hydrophobic interactions). These agents include, but not limited to gemcitabine, methotrexate, platinum-based drugs, such as cisplatin or oxaliplatin, and Anthracycline family drugs such as doxorubicin, daunorubicine, idarubicine, and epirubicine, just for example.

Figure 27:
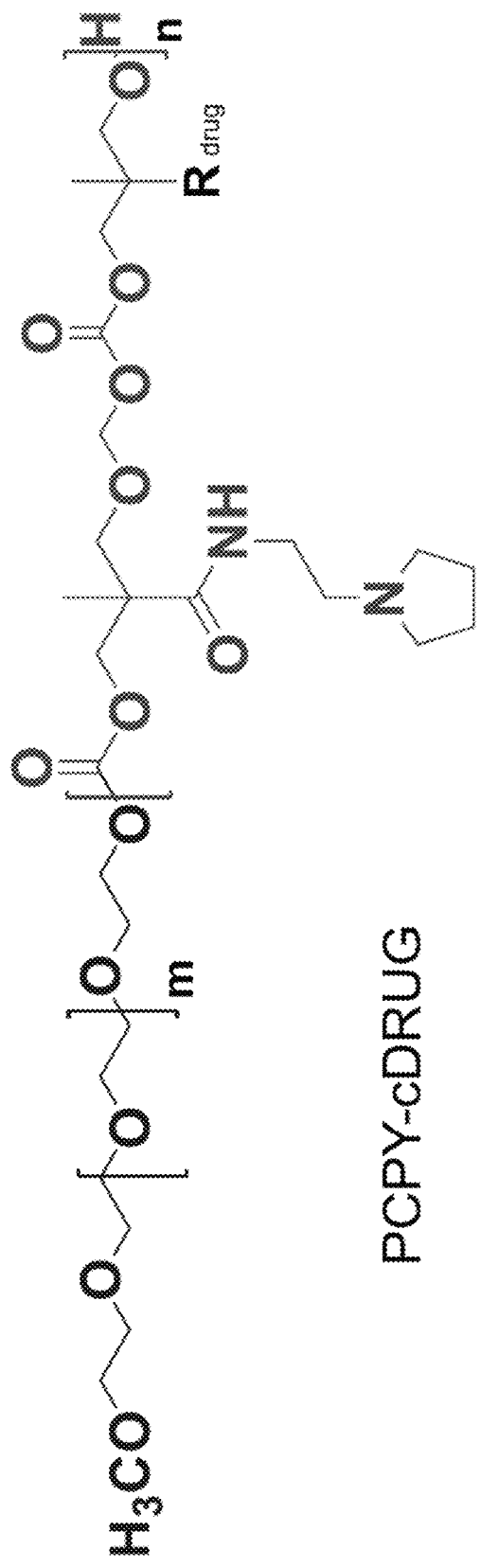
FIG. 27 is a schematic of a generic model of a PCPY-cDRUG.

FURTHER EMBODIMENTS: Referring to FIG. 27, for the candidates the inventors frequently and conveniently synthesized (under regular room temperature, pressure and atmospheric conditions) m was fixed, e.g., m=114 and n values varied between 14-30. By changing the length of PEG, m value can be changed down to m=100, 86, or 50, for example, and all the way to m=128, 142, 180, 200, and 227. Similarly, the length of the second block, that is the value of n, can be decreased readily to 12, 10, or 5, for example, and by maintaining rigorous inert conditions, further lengthening of second block, that is, the value of n, can be increased all the way to 40, 50, 75, and 100. Such increment of m and n, increases the molecular weight (in g/mol or Dalton basis). If one goes out of this ranges, the polymers show reduced solubility and forms relatively larger sized nanoparticles (>150 nm). However, the drug loading capacity is increased with increasing m.w. of the polymer, which might be useful for many applications, such as designing polymer-based devices, and such larger sized nanoparticles are contemplated as part of this invention. Such values of polymer are anticipated as being produced conjugated to the chemotherapeutic, and also produced independent of the chemotherapeutic for conjugation at a later point in time.

In these polymers, variegated structural constructs can be included, and the construct will still function, though likely at a reduced functionality. The function, solubility, materials property and toxicity will change due to such structural modification. For example, one can include C—C chains between the $R_{drug}$ and polymer backbone (red structure in FIG. 27), or between the amine trigger (green structure in FIG. 27) and the polymer backbone. The length of polymers, (e.g., m and n value) can also be changed to a degree with minimal affect to properties. A change in the placement of the double bonded oxygen between the $R_{drug}$ and the amine trigger to another carbon on teh polymer backbone that separates the $R_{drug}$ and the amine trigger is also contemplated, as it is not expected diminish functionality of the construct to that large of a degree, other likely changing the degradation pattern of the polymer axis or backbone.

Pharmaceutical Compositions

The methods described herein can also include the administrations of pharmaceutically acceptable compositions that include the therapeutic, or a pharmaceutically acceptable salt, solvate, or prodrug thereof, conjugated to a nanocarrier as described herein. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered with the nanocarrier alone, or in a mixture, in the presence of an additional pharmaceutically acceptable excipient or carrier. The excipient or carrier is selected on the basis of the mode and route of administration and such that the therapeutic effect of the chemotherapeutic nanocarrier conjugate is not substantially diminished. Suitable pharmaceutical carriers, as well as pharmaceutical necessities for use in pharmaceutical formulations, are described in *Remington: The Science and Practice of Pharmacy*, 22$^{nd}$ Ed., Gennaro, Ed., Lippencott Williams & Wilkins (2012), a well-known reference text in this field, and in the USP/NF (United States Pharmacopeia and the National Formulary), each of which is incorporated by reference. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Excipients, in addition to the nanocarrier, may include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients*, 8$^{th}$ Edition, Sheskey et al., Eds., Pharmaceutical Press (2017), which is incorporated by reference.

The methods described herein can include the administration of a therapeutic, or prodrugs or pharmaceutical compositions thereof, or other therapeutic agents.

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion-controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Parenteral Administration

Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 μm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery

Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences,* 81(1): 1-10, 1992).

Oral transmucosal absorption is generally rapid because of the rich vascular supply to the mucosa and allows for a rapid rise in blood concentrations of the therapeutic.

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art (see, e.g., Biesalski, U.S. Pat. No. 5,112,598, and Biesalski, U.S. Pat. No. 5,556,611).

Formulations for sublingual administration can also be used, including powders and aerosol formulations. Exemplary formulations include rapidly disintegrating tablets and liquid-filled soft gelatin capsules.

Dosing Regimes

The present methods for treating cancer are carried out by administering a therapeutic for a time and in an amount sufficient to result in decreased cancer growth or decreased cancer size, for example.

The amount and frequency of administration of the compositions can vary depending on, for example, what is being administered, the state of the patient, and the manner of administration. In therapeutic applications, compositions can be administered to a patient suffering from cancer in an amount sufficient to relieve or least partially relieve the symptoms of the cancer and its complications. The dosage is likely to depend on such variables as the type and extent of progression of the cancer, the severity of the cancer, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of the cancer or slowing its progression.

The amount of therapeutic per dose can vary. For example, a subject can receive from about 0.1 μg/kg to about 10,000 μg/kg. Generally, the therapeutic is administered in an amount such that the peak plasma concentration ranges from 150 nM-250 μM.

Exemplary dosage amounts can fall between 0.1-5000 μg/kg, 100-1500 μg/kg, 100-350 μg/kg, 340-750 μg/kg, or 750-1000 μg/kg. Exemplary dosages can 0.25, 0.5, 0.75, 1°, or 2 mg/kg. In another embodiment, the administered dosage can range from 0.05-5 mmol of therapeutic (e.g., 0.089-3.9 mmol) or 0.1-50 μmol of therapeutic (e.g., 0.1-25 μmol or 0.4-20 μmol).

The plasma concentration of therapeutic can also be measured according to methods known in the art. Exemplary peak plasma concentrations of therapeutic can range from 0.05-10 μM, 0.1-10 μM, 0.1-5.0 μM, or 0.1-1 μM. Alternatively, the average plasma levels of therapeutic can range from 400-1200 μM (e.g., between 500-1000 μM) or between 50-250 μM (e.g., between 40-200 μM). In some embodiments where sustained release of the drug is desirable, the peak plasma concentrations (e.g., of therapeutic) may be maintained for 6-14 hours, e.g., for 6-12 or 6-10 hours. In other embodiments where immediate release of the drug is desirable, the peak plasma concentration (e.g., of therapeutic) may be maintained for, e.g., 30 minutes.

The frequency of treatment may also vary. The subject can be treated one or more times per day with therapeutic (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits

Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce symptoms and/or underlying cause of the cancer.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A pharmaceutical composition comprising a chemotherapeutic, or any pharmaceutically acceptable salt, solvate, or prodrug thereof, covalently conjugated to a poly(ethylene glycol)-b-poly(carbonate) (PEG-PC) block copolymer nanocarrier;
   wherein the chemotherapeutic has a primary (1°) amine (—NH2) group within a pharmaceutical structure of the chemotherapeutic structure.

2. The pharmaceutical composition of claim 1 wherein the chemotherapeutic is one of gemcitabine, methotrexate, doxorubicin, daunorubicine, idarubicine, and epirubicine.

3. The pharmaceutical composition of claim 1 wherein the nanocarrier contains a 2-pyrrolidine-1-yl-ethyl-amine and a polycarbonate.

4. The pharmaceutical composition of claim 1, wherein the chemotherapeutic is doxorubicin.

5. The pharmaceutical composition of claim 1 wherein the nanocarrier is a pH-sensitive nanocarrier.

6. The pharmaceutical composition of claim 1 wherein the nanocarrier releases the chemotherapeutic substantially only in an acidic environment.

7. The pharmaceutical composition of claim 1 wherein the nanocarrier releases the chemotherapeutic preferentially at a pH of 5.5 compared to a pH of 7.4.

8. The pharmaceutical composition of claim 1 wherein the chemotherapeutic is not encapsulated.

9. The pharmaceutical composition of claim 1 wherein the chemotherapeutic nanocarrier conjugate has a positive surface charge.

10. The pharmaceutical composition of claim 1 wherein the chemotherapeutic nanocarrier conjugate has a tertiary amine trigger.

11. A pharmaceutical composition comprising:
    a chemotherapeutic covalently conjugated to a pH-sensitive nanocarrier by a conditionally unstable amide bond;
    wherein the chemotherapeutic is one of gemcitabine, methotrexate, cisplatin, oxaliplatin, doxorubicin, daunorubicine, idarubivine, and epirubicine, or any pharmaceutically acceptable salt, solvate, or prodrug thereof, and the nanocarrier contains a 2-pyrrolidine-1-yl-ethyl-amine and a polycarbonate.

12. A pharmaceutical composition comprising a chemotherapeutic, or any pharmaceutically acceptable salt, solvate, or prodrug thereof, covalently conjugated to a poly(ethylene glycol)-b-poly(carbonate) (PEG-PC) block copolymer nanocarrier by a conditionally unstable amide bond.

* * * * *